US009511153B2

(12) United States Patent
Harder et al.

(10) Patent No.: US 9,511,153 B2
(45) Date of Patent: Dec. 6, 2016

(54) LOADABLE POLYMERIC PARTICLES FOR THERAPEUTIC AND/OR DIAGNOSTIC APPLICATIONS AND METHODS OF PREPARING AND USING THE SAME

(71) Applicant: CeloNova BioSciences Germany GmbH, Ulm (DE)

(72) Inventors: Philipp Harder, Heidelberg (DE); Olaf Fritz, Hirschhorn (DE); Ulf Fritz, Hirschhorn (DE)

(73) Assignee: CeloNova BioSciences Germany GmbH, Ulm (DE)

( * ) Notice: Subject to any disclaimer, the term of this patent is extended or adjusted under 35 U.S.C. 154(b) by 1113 days.

(21) Appl. No.: 13/623,151

(22) Filed: Sep. 20, 2012

(65) Prior Publication Data

US 2013/0052142 A1 Feb. 28, 2013

Related U.S. Application Data

(62) Division of application No. 11/257,535, filed on Oct. 25, 2005, now Pat. No. 8,318,209.

(60) Provisional application No. 60/621,729, filed on Oct. 25, 2004, provisional application No. 60/684,309, filed on May 24, 2005.

(51) Int. Cl.
*A61K 49/00* (2006.01)
*A61K 49/04* (2006.01)
(Continued)

(52) U.S. Cl.
CPC ......... *A61K 49/0419* (2013.01); *A61K 9/1641* (2013.01); *A61K 9/5031* (2013.01); *A61K 9/5073* (2013.01)

(58) Field of Classification Search
None
See application file for complete search history.

(56) References Cited

U.S. PATENT DOCUMENTS 3,949,073 A 4/1976 Daniels et al.
4,107,288 A 8/1978 Oppenheim et al.
(Continued)

FOREIGN PATENT DOCUMENTS

JP 62086024 A 4/1987
WO WO 01/72281 A2 10/2001
(Continued)

OTHER PUBLICATIONS

Jayakrishnan et al., "Hydrogel Microspheres from Crosslinked Poly(methyl methacrylate): Synthesis and Biocompatibility Studies", *Bull. Mater. Sci.*, vol. 12, No. 1, pp. 17-25 (Mar. 1989).
(Continued)

*Primary Examiner* — Paul Dickinson

(57) ABSTRACT

Particles are provided for use in therapeutic and/or diagnostic procedures. The particles include poly[bis(trifluoroethoxy)phosphazene] and/or a derivatives thereof which may be present throughout the particles or within an outer coating of the particles. The particles can also include a core having a hydrogel formed from an acrylic-based polymer. Barium sulfate may also be provided to the core of the particles as a coating or absorbed within the core of the particles. The particles can be used to minimize blood flow to mammalian tissues by occluding at least a portion of a blood vessel of the mammal, or to deliver an active agent to a localized area within a body of a mammal by contacting a localized area with at least one of the particles. Further, the particles are useful in sustained release formulations including active agent(s) for oral administration, as tracer particles for injection into the bloodstream of a mammal or for use in enhanced ultrasound imaging. The particles may include agents for increasing density for achieving useful buoyancy levels in suspension.

4 Claims, 9 Drawing Sheets

(51) Int. Cl.
*A61K 9/16* (2006.01)
*A61K 9/50* (2006.01)

(56) References Cited

U.S. PATENT DOCUMENTS

| | | |
|---|---|---|
| 4,124,705 A | 11/1978 | Rothman et al. |
| 4,166,800 A | 9/1979 | Fong |
| 4,373,217 A | 2/1983 | Draenert |
| 4,424,208 A | 1/1984 | Wallace et al. |
| 4,440,750 A | 4/1984 | Glowacki et al. |
| 4,452,916 A | 6/1984 | Boschetti |
| 4,535,485 A | 8/1985 | Ashman et al. |
| 4,537,916 A | 8/1985 | Bruschtein et al. |
| 4,547,390 A | 10/1985 | Ashman et al. |
| 4,557,764 A | 12/1985 | Chu |
| 4,565,580 A | 1/1986 | Miyata et al. |
| 4,582,640 A | 4/1986 | Smestad et al. |
| 4,592,755 A | 6/1986 | Penton et al. |
| 4,595,713 A | 6/1986 | St. John |
| 4,677,173 A | 6/1987 | Hölle et al. |
| 4,698,373 A | 10/1987 | Tateosian et al. |
| 4,728,570 A | 3/1988 | Ashman et al. |
| 4,803,075 A | 2/1989 | Wallace et al. |
| 4,837,285 A | 6/1989 | Berg et al. |
| 4,849,285 A | 7/1989 | Dillon |
| 4,851,046 A | 7/1989 | Low et al. |
| 4,902,511 A | 2/1990 | Kronman |
| 4,912,141 A | 3/1990 | Kronman |
| 4,999,188 A | 3/1991 | Solodovnik et al. |
| 5,007,940 A | 4/1991 | Berg |
| 5,019,400 A | 5/1991 | Gombotz et al. |
| 5,077,049 A | 12/1991 | Dunn et al. |
| 5,116,387 A | 5/1992 | Berg |
| 5,137,875 A | 8/1992 | Tsunenaga et al. |
| 5,142,008 A | 8/1992 | Hölle et al. |
| 5,143,724 A | 9/1992 | Leshchiner et al. |
| 5,158,573 A | 10/1992 | Berg |
| 5,162,430 A | 11/1992 | Rhee et al. |
| 5,204,382 A | 4/1993 | Wallace et al. |
| 5,258,028 A | 11/1993 | Ersek et al. |
| 5,278,202 A | 1/1994 | Dunn et al. |
| 5,292,802 A | 3/1994 | Rhee et al. |
| 5,294,446 A | 3/1994 | Schlameus et al. |
| 5,304,595 A | 4/1994 | Rhee et al. |
| 5,306,500 A | 4/1994 | Rhee et al. |
| 5,308,701 A | 5/1994 | Cohen et al. |
| 5,324,775 A | 6/1994 | Rhee et al. |
| 5,342,557 A | 8/1994 | Kannedy |
| 5,344,452 A | 9/1994 | Lemperle |
| 5,352,715 A | 10/1994 | Wallace et al. |
| 5,368,859 A | 11/1994 | Dunn et al. |
| 5,395,620 A | 3/1995 | Huc et al. |
| 5,397,352 A | 3/1995 | Burres |
| 5,399,351 A | 3/1995 | Leshchiner et al. |
| 5,413,791 A | 5/1995 | Rhee et al. |
| 5,428,024 A | 6/1995 | Chu et al. |
| 5,446,091 A | 8/1995 | Rhee et al. |
| 5,451,406 A | 9/1995 | Lawin et al. |
| 5,456,693 A | 10/1995 | Conston et al. |
| 5,464,932 A | 11/1995 | Allcock et al. |
| 5,476,666 A | 12/1995 | Rhee et al. |
| 5,487,390 A | 1/1996 | Cohen et al. |
| 5,487,897 A | 1/1996 | Polson et al. |
| 5,494,673 A | 2/1996 | Andrianov et al. |
| 5,494,682 A | 2/1996 | Cohen et al. |
| 5,500,161 A | 3/1996 | Andrianov et al. |
| 5,510,418 A | 4/1996 | Rhee et al. |
| 5,516,532 A | 5/1996 | Atala et al. |
| 5,529,777 A | 6/1996 | Andrianov et al. |
| 5,562,099 A | 10/1996 | Cohen et al. |
| 5,562,909 A | 10/1996 | Allcock et al. |
| 5,571,182 A | 11/1996 | Ersek et al. |
| 5,599,852 A | 2/1997 | Scopelianos et al. |
| 5,624,685 A | 4/1997 | Takahashi et al. |
| 5,633,001 A | 5/1997 | Agerup |
| 5,635,215 A | 6/1997 | Boschetti et al. |
| 5,639,796 A | 6/1997 | Lee |
| 5,648,100 A | 7/1997 | Boschetti et al. |
| 5,681,873 A | 10/1997 | Norton et al. |
| 5,686,425 A | 11/1997 | Lee |
| 5,728,752 A | 3/1998 | Scopelianos et al. |
| 5,733,562 A | 3/1998 | Lee |
| 5,752,974 A | 5/1998 | Rhee et al. |
| 5,763,399 A | 6/1998 | Lee |
| 5,776,193 A | 7/1998 | Kwan et al. |
| 5,824,333 A | 10/1998 | Scopelianos et al. |
| 5,840,290 A | 11/1998 | Hench et al. |
| 5,840,819 A | 11/1998 | Biensan |
| 5,855,895 A | 1/1999 | Andrianov et al. |
| 5,922,025 A | 7/1999 | Hubbard |
| 5,955,143 A | 9/1999 | Wheatley et al. |
| 5,962,427 A | 10/1999 | Goldstein et al. |
| 6,015,563 A | 1/2000 | Andrianov et al. |
| 6,063,061 A | 5/2000 | Wallace et al. |
| 6,066,325 A | 5/2000 | Wallace et al. |
| 6,071,530 A | 6/2000 | Polson et al. |
| 6,083,262 A | 7/2000 | Caravel |
| 6,165,489 A | 12/2000 | Berg et al. |
| 6,190,684 B1 | 2/2001 | Hench et al. |
| 6,207,171 B1 | 3/2001 | Payne et al. |
| 6,210,715 B1 | 4/2001 | Starling et al. |
| 6,214,331 B1 | 4/2001 | Vanderhoff et al. |
| 6,261,323 B1 | 7/2001 | Neto |
| 6,261,573 B1 | 7/2001 | Loebelenz et al. |
| 6,270,748 B1 | 8/2001 | Annan et al. |
| 6,277,392 B1 | 8/2001 | Klein |
| 6,281,015 B1 | 8/2001 | Mooney et al. |
| 6,284,284 B1 | 9/2001 | Naughton |
| 6,309,420 B1 | 10/2001 | Preissman |
| 6,335,028 B1 | 1/2002 | Vogel et al. |
| 6,335,383 B1 | 1/2002 | Scopelianos et al. |
| 6,365,187 B2 | 4/2002 | Mathiowitz et al. |
| 6,383,500 B1 | 5/2002 | Wooley et al. |
| 6,391,343 B1 | 5/2002 | Yen |
| 6,423,332 B1 | 7/2002 | Huxel et al. |
| 6,423,343 B1 | 7/2002 | Lee et al. |
| 6,431,174 B1 | 8/2002 | Knudson et al. |
| 6,432,437 B1 | 8/2002 | Hubbard |
| 6,436,424 B1 | 8/2002 | Vogel et al. |
| 6,458,387 B1 | 10/2002 | Scott et al. |
| 6,458,889 B1 | 10/2002 | Trollsas et al. |
| 6,491,903 B1 | 12/2002 | Forster et al. |
| 6,530,878 B2 | 3/2003 | Silverman et al. |
| 6,531,152 B1 | 3/2003 | Lerner et al. |
| 6,537,574 B1 | 3/2003 | Hubbard |
| 6,544,503 B1 | 4/2003 | Vanderhoff et al. |
| 6,546,936 B2 | 4/2003 | Knudson et al. |
| 6,555,123 B2 | 4/2003 | Williams et al. |
| 6,558,612 B1 | 5/2003 | Hubbard |
| 6,585,994 B2 | 7/2003 | Williams et al. |
| 6,620,185 B1 | 9/2003 | Harvie et al. |
| 6,652,873 B2 | 11/2003 | Deaver et al. |
| 6,660,301 B1 | 12/2003 | Vogel et al. |
| 6,662,805 B2 | 12/2003 | Frondoza et al. |
| 6,666,892 B2 | 12/2003 | Hiles et al. |
| 6,676,971 B2 | 1/2004 | Goupil et al. |
| 6,680,046 B1 | 1/2004 | Boschetti |
| 6,682,760 B2 | 1/2004 | Noff et al. |
| 6,689,823 B1 | 2/2004 | Bellare et al. |
| 6,699,471 B2 | 3/2004 | Radice et al. |
| 6,713,646 B2 | 3/2004 | Zhang et al. |
| 6,767,637 B2 | 7/2004 | Park et al. |
| 6,790,456 B2 | 9/2004 | Vogel et al. |
| 6,858,634 B2 | 2/2005 | Asrar et al. |
| 6,866,860 B2 | 3/2005 | Nathan |
| 6,869,445 B1 | 3/2005 | Johnson |
| 6,872,799 B2 | 3/2005 | Nathan |
| 6,884,905 B2 | 4/2005 | Zhang et al. |
| 6,916,910 B2 | 7/2005 | Wolfinbarger, Jr. |
| 6,933,326 B1 | 8/2005 | Griffey et al. |
| 6,936,271 B1 | 8/2005 | Oliver et al. |
| 6,949,251 B2 | 9/2005 | Dalal et al. |
| 6,962,979 B1 | 11/2005 | Rhee |
| 6,967,234 B2 | 11/2005 | Nathan |

(56) References Cited

U.S. PATENT DOCUMENTS

| | | |
|---|---|---|
| 7,004,977 B2 | 2/2006 | Ashman |
| 7,012,126 B2 | 3/2006 | Matsuda et al. |
| 7,025,980 B1 | 4/2006 | Williams et al. |
| 7,025,990 B2 | 4/2006 | Sawhney |
| 7,026,374 B2 | 4/2006 | Nathan et al. |
| 7,053,134 B2 | 5/2006 | Baldwin et al. |
| 7,053,209 B1 | 5/2006 | Gibson et al. |
| 7,056,277 B2 | 6/2006 | Silverman et al. |
| 7,057,019 B2 | 6/2006 | Pathak |
| 7,060,287 B1 | 6/2006 | Hubbard et al. |
| 7,060,298 B2 | 6/2006 | Vogel et al. |
| 7,077,144 B2 | 7/2006 | Knudson et al. |
| 7,094,369 B2 | 8/2006 | Buiser et al. |
| 7,129,209 B2 | 10/2006 | Rhee |
| 7,131,997 B2 | 11/2006 | Bourne et al. |
| 7,135,593 B2 | 11/2006 | Zhang et al. |
| 7,144,414 B2 | 12/2006 | Harvie et al. |
| 7,157,080 B2 | 1/2007 | Radice et al. |
| 7,160,931 B2 | 1/2007 | Cheng et al. |
| 7,192,984 B2 | 3/2007 | Berg et al. |
| 7,244,270 B2 | 7/2007 | Lesh |
| 7,249,601 B2 | 7/2007 | Silverman et al. |
| 7,288,319 B2 | 10/2007 | Baldwin et al. |
| 7,303,756 B1 | 12/2007 | Bodmeier |
| 7,314,636 B2 | 1/2008 | Caseres et al. |
| 7,326,172 B2 | 2/2008 | Miller |
| 7,338,657 B2 | 3/2008 | Vogel et al. |
| 2002/0016637 A1 | 2/2002 | Anton |
| 2002/0068089 A1 | 6/2002 | Vogel et al. |
| 2002/0151466 A1 | 10/2002 | Hubbard et al. |
| 2002/0197326 A1 | 12/2002 | Vogel et al. |
| 2003/0099683 A1 | 5/2003 | Grunze |
| 2003/0140930 A1 | 7/2003 | Knudson et al. |
| 2003/0149490 A1 | 8/2003 | Ashman |
| 2003/0153806 A1 | 8/2003 | Miller |
| 2003/0171646 A1 | 9/2003 | Pratt et al. |
| 2003/0215519 A1 | 11/2003 | Schwarz et al. |
| 2004/0020497 A1 | 2/2004 | Knudson et al. |
| 2004/0028676 A1 | 2/2004 | Klein et al. |
| 2004/0047892 A1 | 3/2004 | Desrosiers et al. |
| 2004/0091425 A1 | 5/2004 | Boschetti |
| 2004/0096514 A1 | 5/2004 | Vogel et al. |
| 2004/0117033 A1 | 6/2004 | Frondoza et al. |
| 2004/0142465 A1 | 7/2004 | Radice et al. |
| 2004/0185021 A1 | 9/2004 | Hubbard |
| 2004/0187878 A1 | 9/2004 | Knudson et al. |
| 2004/0210230 A1 | 10/2004 | Furlow, Jr. |
| 2004/0241203 A1 | 12/2004 | Shakesheff et al. |
| 2005/0025708 A1 | 2/2005 | Vogel et al. |
| 2005/0037047 A1 | 2/2005 | Song |
| 2005/0136093 A1 | 6/2005 | Denk |
| 2005/0165203 A1 | 7/2005 | Kohn et al. |
| 2005/0208095 A1 | 9/2005 | Hunter et al. |
| 2005/0234210 A1 | 10/2005 | Andrianov et al. |
| 2006/0067883 A1 | 3/2006 | Krom et al. |
| 2006/0088476 A1 | 4/2006 | Harder et al. |
| 2006/0240064 A9 | 10/2006 | Hunter et al. |
| 2006/0251582 A1 | 11/2006 | Reb |
| 2006/0251697 A1 | 11/2006 | Li et al. |
| 2007/0003503 A1 | 1/2007 | Sabetsky |
| 2007/0003584 A1 | 1/2007 | Anderson |
| 2007/0077544 A1 | 4/2007 | Lemperle et al. |
| 2007/0100449 A1 | 5/2007 | O'Neil et al. |
| 2007/0191964 A1 | 8/2007 | Preissman |
| 2007/0240725 A1 | 10/2007 | McKay |
| 2008/0015498 A1 | 1/2008 | Lesh |
| 2008/0058954 A1 | 3/2008 | Trieu |

FOREIGN PATENT DOCUMENTS

| | | |
|---|---|---|
| WO | WO-2004/004795 A1 | 1/2004 |
| WO | WO 2006/046155 A2 | 5/2006 |

OTHER PUBLICATIONS

Hart et al., "Poly(methylmethacrylate) Suspension Polymer", *Macromolecular Syntheses*, Collective vol. 1, pp. 23-25.

Huang et al., "Long-term biocompatibility evaluation of a novel polymer-coated stent in a porcine coronary stent model", *Coronary Artery Disease*, 2003, vol. 14, No. 5, pp. 401-408.

Rao et al., "Hydrolysed Microspheres From Cross-Linked Polymethyl Methacrylate (Hydrogel)", *J. Neuroradiol*, 1991 vol. 18, pp. 61-69.

Richter et al., "A New Polymer Concept for Coating of Vascular Stents Using PTFEP (poly(bis(trifluoroethoxy)phosphazene) to Reduce Thrombogenicity and Late In-Stent Stenosis", *Investigative Radiology*, Apr. 2005, vol. 40, No. 4, pp. 210-218.

Phadke et al., "Embolization of Criminal/Spinal Tumors and Vascular Malformations with Hydrogel Microspheres", *Acta Radiologica*, 2002, vol. 43, pp. 15-20.

Thanoo et al., "Preparation of Hydrogel Beads from Crosslinked Poly(Methyl Methacrylate) Microspheres by Alkaline Hydrolysis", *J. Appl. P. Sci.*, vol. 39, pp. 1153-1161 (1990) (abstract only).

First Examination Report dated Jul. 23, 2013, Application No. 2982/DELNP/2007 filed Apr. 20, 2007, Government of India Patent Office.

First Examination Report dated Jan. 28, 2015, Application No. 653/DELNP/2010 filed Jan. 29, 2010, Government of India Patent Office.

LOADABLE POLYMERIC PARTICLES FOR THERAPEUTIC AND/OR DIAGNOSTIC APPLICATIONS AND METHODS OF PREPARING AND USING THE SAME

CROSS-REFERENCE TO RELATED APPLICATIONS

This application is a divisional of U.S. Ser. No. 11/257,535, filed Oct. 25, 2005 which claims the benefit of priority under 35 U.S.C. §119(e) of U.S. Provisional Patent Applications No. 60/684,307, filed May 24, 2005 and 60/621,729, filed Oct. 25, 2004, the entire disclosures of which are incorporated herein by reference in their entirety.

BACKGROUND OF THE INVENTION

Small particles, including microspheres and nanospheres, have many medical uses in diagnostic and therapeutic procedures. Most prior art particles used in medical applications are characterized by numerous disadvantages including irritation of the tissues with which they come in contact and initiation of adverse immune reactions.

Additionally, many of the materials used to prepare the prior art particles may degrade relatively rapidly within the mammalian body, thereby detracting from their utility in certain procedures where long term presence of intact particles may be necessary. Moreover, the degradation of the prior art materials may release toxic or irritating compounds causing adverse reactions in the patients.

It is also a problem in the art for certain types of prior art particles that it is difficult to achieve desirable suspension properties when the particles are incorporated into a delivery suspension for injection into a site in the body to be treated. Many times, the particles settle out or tend to "float" in the solution such that they are not uniformly suspended for even delivery. Furthermore, particles may tend to aggregate or agglomerate within the delivery solution and/or adhere to some part of the delivery device, making it necessary to compensate for these adhesive/attractive forces.

In order to achieve a stable dispersion, it is known to add suitable dispersing agents that may include surfactants directed at breaking down attractive particle interaction. Depending on the nature of the particle interaction, the following materials may be used: cationic, anionic or non-ionic surfactants such as Tween™ 20, Tween™ 40, Tween™ 80, polyethylene glycols, sodium dodecyl sulfate, various naturally occurring proteins such as serum albumin, or any other macromolecular surfactants in the delivery formulation. Furthermore thickening agents can be used help prevent particles from settling by sedimentation and to increase solution viscosity, for example, polyvinyl alcohols, polyvinyl pyrrolidones, sugars or dextrins. Density additives may also be used to achieve buoyancy.

It can also be difficult to visualize microparticles in solution to determine their degree of suspension when using clear, transparent polymeric acrylate hydrogel beads in aqueous suspension.

Attempts to use the inert precipitate, barium sulfate, in particle form is known as an additive for bone cement, for silicones for rendering items visible during X-ray examination and for providing radiopacity to polymeric acrylate particles. See Jayakrishnan et al., *Bull. Mat. Sci.*, Vol. 12, No. 1, pp. 17-25 (1989). The barium sulfate also is known for improving fluidization, and is often used as an inorganic filler to impart anti-stick behavior to moist, aggregated particles. Other prior art attempts to increase visualization of microparticles include use of gold, for example, Embosphere Gold™ provides a magenta color to acrylate microparticles using small amounts of gold.

There thus exists in the art a need for small particles that can be formed to have a preferential generally spherical configuration for certain applications such as various therapeutic and diagnostic procedures which are not degraded by the natural systems of the mammalian system, are biocompatible, resist clumping, are easy to visualize in suspension while in use and/or demonstrate acceptable physical and suspension properties.

BRIEF SUMMARY OF THE INVENTION

The invention includes a particle for use in a therapeutic and/or diagnostic procedure. The particle comprises poly[bis(trifluoroethoxy)phosphazene] and/or a derivative thereof.

Also included is a method of minimizing blood flow to a tissue in a mammal comprising occluding at least a portion of a blood vessel of the mammal with at least one particle, wherein the particle comprises a poly[bis(trifluoroethoxy)phosphazene] and/or a derivative thereof.

Further described herein is a method of delivering an active agent to a localized area within a body of a mammal comprising contacting the localized area with at least one of a particle comprising poly[bis(trifluoroethoxy)phosphazene] and/or a derivative thereof and an active agent, such that an effective amount of the active agent is exposed to the localized area.

Also within the invention is a sustained release formulation of an active agent for oral administration, the formulation comprising a polymer capsule and an active agent, wherein the polymeric capsule comprises poly[bis(trifluoroethoxy)phosphazene] and/or a derivative thereof.

The invention further includes a method of tracing the passage of a particle through a blood vessel in a mammal, the method comprising injecting into the bloodstream of a mammal at least one tracer particle, the tracer particle comprising poly[bis(trifluoroethoxy)phosphazene] and/or a derivative thereof and a contrast agent, and imaging the route of the particle.

Additionally, a method of enhanced ultrasound imaging is described herein. The method comprises administering to an ultrasound subject at least one hollow microcapsule comprising poly[bis(trifluoroethoxy)phosphazene] and/or a derivative thereof to an area of the ultrasound subject, and imaging the area of the subject using ultrasound.

The invention also includes a method of delivering an active agent to a localized area within the body of a mammal comprising contacting the localized area with at least one of a particle comprising poly[bis(trifluoroethoxy)phosphazene] and/or a derivative thereof and an active agent, such that an effective amount of the active agent is exposed to the localized area, wherein the particle comprises an agent to increase density.

Further, a method for minimizing agglomeration and/or aggregation of particles formed from acrylic-based polymers is described in which the method comprises providing barium sulfate to the core and/or surface of the particles.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments that are presently preferred. It should be understood, however, that the invention is not limited to the precise arrangements and instrumentalities shown.

In the drawings:

FIG. 3A shows a 4× optical microscope view and FIG. 3B shows a 100× scanning electron microscope view;

FIG. 5A is an image obtained using an atomic force microscope and FIG. 5B is a scanning electron micrograph showing the surface of an unloaded polyphosphazene microsphere at 5000× magnification;

FIGS. 6 and 7 show a cryoextraction setup for use in an embodiment of the invention wherein FIG. 6 is a cryoextraction vessel and FIG. 7 is a syringe pump;

FIG. 11A is a 50× magnification of a minor amount of delamination in the strong white contrast portion. FIG. 11B is a 200× magnification of the microparticles of FIG. 11A. FIGS. 11C and 11D are, respectively, 200× and 1.0K× magnified SEMs of other Sample C microparticles showing only minor defects.

DETAILED DESCRIPTION OF THE INVENTION

Figure 1:
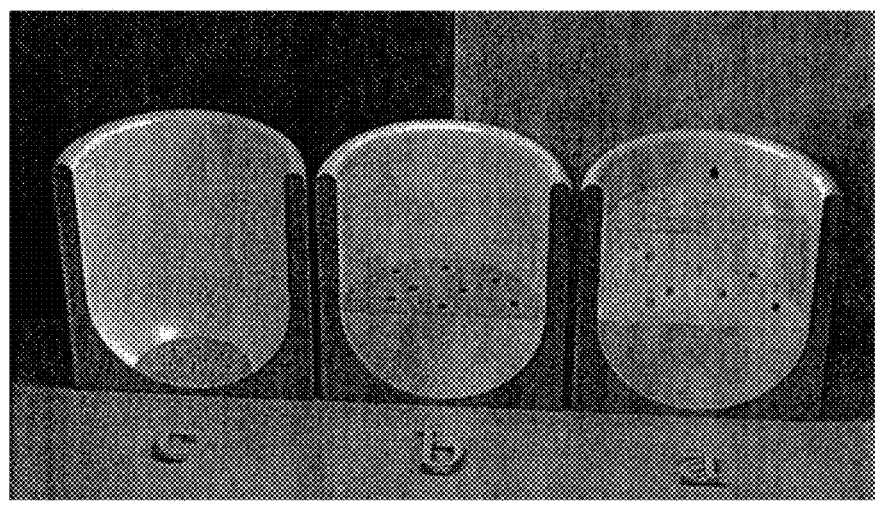
FIG. 1 shows a schematic representation of a general cryoextraction scheme used to prepare particles according to one embodiment of the invention.

Described herein are particles that may be manufactured using poly[bis(trifluoroethoxy)phosphazene] and/or derivatives thereof, as well as methods of preparing such particles. Additionally, described herein are therapeutic and/or diagnostic methods and procedures which use the particles as described herein, including methods of embolization using the particles, methods of delivery of an active agent using the particle (either orally or locally), methods of tracing or visualizing blood or other biological fluids through the body using the particles, and methods of enhanced ultrasound (sonography) using the particles.

Also included are sustained release drug delivery formulations for oral administration including the particles for localized delivery of an active agent to the gastrointestinal system and/or systemic delivery of an active agent as well as a sustained release drug delivery formulation that can be injected subcutaneously or intravenously for localized delivery of an active agent.

All of the methods, compositions and formulations of the invention utilize at least one particle as described herein. "Particle" and "particles" as used herein mean a substantially spherical or ellipsoid article(s), hollow or solid, that may have any diameter suitable for use in the specific methods and applications described below, including a microsphere(s) and a nanosphere(s), beads and other bodies of a similar nature known in the art.

The preferred particles of the invention according to one embodiment described herein are composed, in whole or in part, the specific polyphosphazene polymer known as poly [bis(trifluoroethoxy)phosphazene] or a derivative of poly [bis(trifluoroethoxy)phosphazene]. Use of this specific polymer provides particles that are at least in part inorganic in that they include an inorganic polymer backbone and which are also biocompatible in that when introduced into a mammal (including humans and animals), they do not significantly induce a response of the specific or non-specific immune systems. The scope of the invention also includes the use(s) of such particles as controlled drug delivery vehicles or tracer particles for the visualization of blood vessels and other organs.

The particles are useful in a variety of therapeutic and/or diagnostic procedures in part because they can be prepared in sizes large enough to occlude a blood vessel as well as small enough to easily pass through the smaller vessels, e.g., visualization or drug delivery purposes. Additionally, owing to the biocompatible nature of the polymer, the particles facilitate avoidance or elimination of immunogenic reactions generally encountered when foreign bodies are introduced into a mammalian body, such as "implant rejection" or "allergic shock," and other adverse reactions of the immune system. Moreover, it has been found that the particles of the invention exhibit reduced biodegradation in vivo, thereby increasing the long-term stability of the particle in the biological environment. Moreover, in those situations where some degradation is undergone by the polymer in the particle, the products released from the degradation include only non-toxic concentrations of phosphorous, ammonia, and trifluoroethanol, which, advantageously, is known to promote anti-inflammatory responses when in contact with mammalian tissue.

Each of the particles in the invention is formed in part of the polymer, poly[bis(2,2,2-trifluoroethoxy)phosphazene] or a derivative thereof (referred to further herein as either "poly[bis(trifluoroethoxy)phosphazene]" or "PTFEP"). The preferred poly[bis(trifluoroethoxy)phosphazene] polymer is made up of repeating monomers represented by the formula (I) shown below:

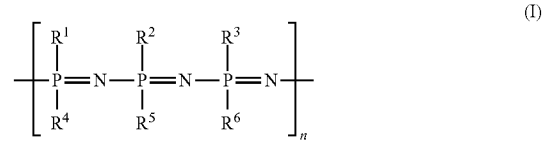

wherein $R^1$ to $R^6$ are all trifluoroethoxy ($OCH_2CF_3$) groups and n may vary from at least about 100 to larger molecular weight lengths, preferably n is about 4,000 to about 300,000, more preferably, n is about 4,000 to about 3,000 and most preferably n is about 13,000 to about 30,000. Alternatively, one may use derivatives of this polymer in the preparation of the particles of the invention. By "derivatives," it is meant polymers made up of monomers having the structure of formula (I) but where one or more of the $R^1$-$R^6$ functional groups or backbone atom(s) is substituted by a different atom(s) or functional group(s), but where the biological inertness of the polymer is not substantially altered. Exemplary functional groups include ethoxy ($OCH_2CH_3$), 2,2,3,3-pentafluoropropyloxy ($OCH_2CF_2CF_3$), 2,2,2,2',2',2'-hexafluoroisopropyloxy ($OCH(CF_3)_2$), 2,2,3,3,4,4,4-heptafluorobutyloxy ($OCH_2CF_2CF_2CF_3$), 3,3,4,4,5,5,6,6,7,7,8,8,8-tridecafluorooctyloxy ($OCH_2(CF_2)_7CF_3$), 2,2,3,3,-tetrafluoropropyloxy ($OCH_2CF_2CHF_2$), 2,2,3,3,4,4-hexafluorobutyloxy ($OCH_2CF_2CF_2CF_3$), 3,3,4,4,5,5,6,6,7,7,8,8-dodecafluorooctyloxy ($OCH_2(CF_2)_7CHF_2$). Further, in some embodiments, 1% or less of the $R^1$ to $R^6$ groups may be alkenoxy groups that assist crosslinking in order to provide a more elastomeric phosphazene polymer, including groups such as $OCH_2CH{=}CH_2$, $OCH_2CH_2CH{=}CH_2$ or allylphenoxy groups.

It is preferred that the molecular weight of the polymer used to prepare the particles of the invention has a molecular weight based on the above formula, and more preferably, a molecular weight of at least about 70,000 g/mol, more preferably at least about 1,000,000 g/mol, and still more preferably a molecular weight of at least about $3 \times 10^6$ g/mol to about $20 \times 10^6$ g/mol. Most preferred are polymers having molecular weights of at least about 10,000,000 g/mol.

The diameter of a particle formed according to the invention will necessarily vary depending on the end application in which the particle is to be used. The diameter of such particles is preferably about 1 to about 5,000 μm, with a diameter of about 1 to about 1,000 μm being most preferred. Other common sizes include diameters of about 200 to about 500 μm, about 1 to about 200 μm and greater than about 500 μm, however, it should be understood based on this disclosure that various combinations of particles sizes and various ranges within the broader range of from about 1 to about 5,000 μm are within the scope of this disclosure. In methods using the particle where more than one particle is preferred it is not necessary that all particles be of the same diameter or shape. However, in accordance with the invention precisely calibrated particles may be prepared having exemplary ranges as follows:

100 μm±25 μm
250 μm±50 μm
400 μm±50 μm
500 μm±50 μm
700 μm±50 μm
900 μm±50 μm

It is also within the scope of the invention that various ranges such as those noted above could be prepared and combined for blended applications, for example, particles in ranges from 500 to 700 μm.

The particles may also include other compounds which function to enhance, alter or otherwise modify the behavior of the polymer or particle either during its preparation or in its therapeutic and/or diagnostic use. For example, active agents such as peptides, proteins, hormones, carbohydrates, polysaccharides, nucleic acids, lipids, vitamins, steroids and organic or inorganic drugs may be incorporated into the particle. Excipients such as dextran, other sugars, polyethylene glycol, glucose, and various salts, including, for example, chitosan glutamate, may be included in the particle.

Additionally, if desired, polymers other than the poly[bis (trifluoroethoxy)phosphazene] and/or its derivative may be included with in the particle. Examples of polymers may include poly(lactic acid), poly(lactic-co-glycolic acid), poly (caprolactone), polycarbonates, polyamides, polyanhydrides, polyamino acids, polyorthoesters, polyacetals, polycyanoacrylates, and polyurethanes. Other polymers include polyacrylates, ethylene-vinyl acetate co-polymers, acyl substituted cellulose acetates and derivatives thereof, degradable or non-degradable polyurethanes, polystyrenes, polyvinylchloride, polyvinyl fluoride, poly(vinyl imidazole), chlorosulphonated polyolefins, and polyethylene oxide. One may incorporate the selected compounds by any means known in the art, including diffusing, inserting or entrapping the additional compounds in the matrix of an already formed particle or by adding the additional compound to a polymer melt or to a polymer solvent in the preparation of the particle such as described herein.

The loaded or unloaded particle may be coated with an additional polymer layer or layers, including polymers such as those mentioned hereinabove. Further, PTFEP or its derivatives may be used to form such a coating on a particle formed of other suitable polymers or copolymers known or to be developed in the art that are used to form particles as described herein. Preferably, when coating a particle such as a microparticle, PTFEP is applied as a coating on a microparticle(s) formed of an acrylic-based polymer as set forth in further detail below.

Coatings are beneficial, for example, if the particle(s) are to be used in a sustained release, orally administered, drug delivery formulation (enteric coating) or if the particles are to be loaded with a potentially toxic contrast agent (non-biodegradable coating).

The microspheres may be prepared by any means known in the art that is suitable for the preparation of particles containing poly[bis(trifluoroethoxy)phosphazene]. In a procedure according to an embodiment herein a "polymer solution" is prepared by mixing one or more polymer solvent(s) and the PTFEP and/or a derivative thereof until the polymer is dissolved.

Suitable solvents for use in the preparation of the polymer solution include any in which the polymer PTFEP and/or its derivatives are soluble. Exemplary solvents include, without limitation, ethyl-, propyl-, butyl-, pentyl-, octylacetate, acetone, methylethylketone, methylpropylketone, methyl-isobutylketone, tetrahydrofurane, cyclohexanone, dimethylacetamide, acetonitrile, dimethyl ether, hexafluorobenzene or combinations thereof.

The polymer solution contains the PTFEP and/or its derivative polymer in a concentration of about 1% by weight of polymer to 20% by weight of polymer, preferably about 5% to 10% by weight of polymer. Other polymers, as discussed above, may be present in the solution, or may be added to the vessel in the form of a second solution powder or other form, if one wishes to include such polymers in the final particle.

In carrying out the process, the polymer solution is next dispensed, preferably in the form of drops or an aerosol, into a vessel containing a non-solvent. By "non-solvent" it is meant any organic or inorganic solvents that do not substantially dissolve the PTFEP polymer and which have a melting point that is lower relative to the melting point of the solvent in which the polymer is dissolved ("polymer solvent"), so that the non-solvent thaws before the solvent thaws in the course of the incubation step. Preferably, this difference between the melting point of the non-solvent and the polymer solvent is about 10° C., more preferably about 15° C., and most preferably, greater than about 20° C. Under certain conditions it has been found that the structural integrity of the resultant particle may be enhanced if the difference of the melting points of the polymer solvent and of the non-solvent is greater than 15° C. However, it is sufficient that the non-solvent point is merely slightly lower than that of the polymer solvent.

The non-solvent/polymer solvent combination is incubated for approximately 1 to 5 days or until the polymer solvent has been completely removed from the particles. While not wishing to be bound by theory, it is hypothesized that during the incubation, the non-solvent functions to extract the polymer solvent from the microscopic polymer solution droplets from the particles such that the polymer is at least gelled. As the incubation period passes, the droplets will shrink and the solvent becomes further extracted, leading to a hardened outer polymeric shell containing a gelled polymer core, and finally, after completion of the incubation, a complete removal of the residual solvent. To ensure that the polymeric droplets retain a substantially spherical shape during the incubation period, they must be in a frozen or substantially gelled state during most if not all of the incubation period. Therefore, the non-solvent temperature may stay below the melting point of the solvent during the cryoextraction process.

As shown in FIG. 1, at the vessel labeled (a), polymer solution droplets are shown being dispensed either with a syringe or other device at a controlled rate onto a top layer of liquid nitrogen. The nitrogen layer is situated over a bottom layer consisting of the selected non-solvent, which will eventually serve to extract the solvent from the frozen polymer solution droplets. The non-solvent layer has been previously frozen with liquid nitrogen prior to the dispensing of the polymer solution. The vessel labeled (b) shows the onset of the dewing of the frozen nonsolvent, into which the frozen polymeric droplets will sink. The vessel labeled (c) shows the cryoextraction procedure after approximately three days of incubation wherein the polymer solution droplets, incubated within the non-solvent, have been depleted of a substantial amount of solvent. The result is a gelled, polymeric particle in the form of a bead having a hardened outer shell. As can be seen by the representation, the non-solvent height within the vessel is slightly reduced due to some evaporation of the non-solvent. The size of the beads will shrink quite substantially during this process depending on the initial concentration of the polymer in the polymer solution.

Figure 2:
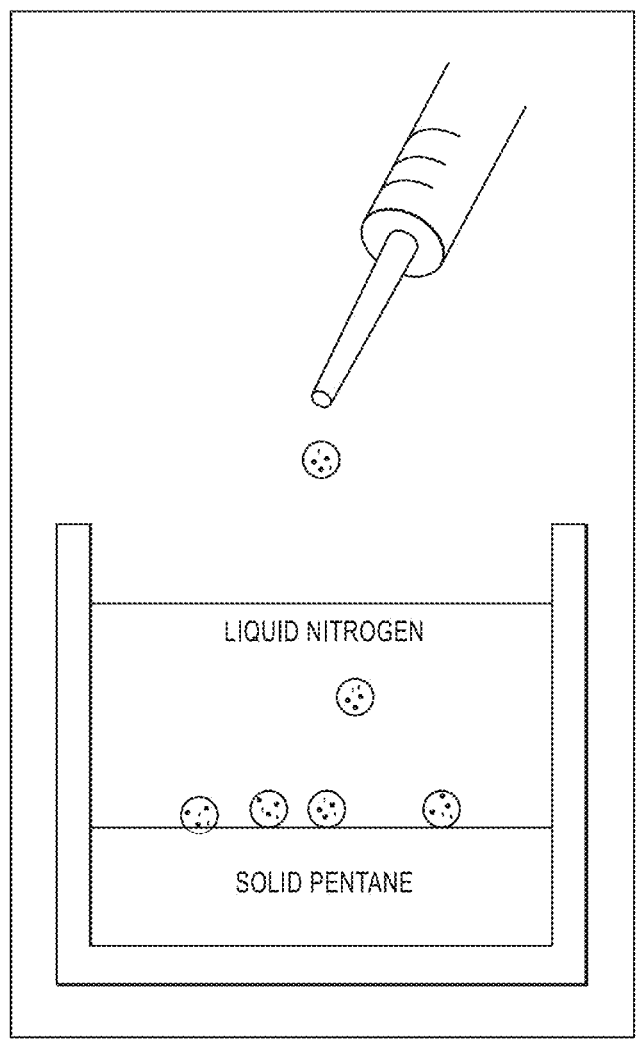
FIG. 2 shows the manual dripping technique by which the polymer solution was supplied to liquid nitrogen in preparation of the microspheres of Example 1, herein.

In one embodiment of a method of preparing a PTFEP-containing particle(s) according to the invention, such particles can be formed using any way known or to be developed in the art. Two exemplary preferred methods of accomplishing this include wherein (i) the non-solvent residing in the vessel in the method embodiment described above is cooled to close to its freezing point or to its freezing point prior to the addition of the polymer solution such that the polymer droplets freeze upon contact with the pre-cooled non-solvent; or (ii) the polymer droplets are frozen by contacting them with a liquefied gas such as nitrogen, which is placed over a bed of pre-frozen non-solvent (see, FIG. 2). In method (ii), after the nitrogen evaporates, the non-solvent slowly thaws and the microspheres in their frozen state will sink into the liquid, cold non-solvent where the extraction process (removal of the polymer solvent) will be carried out.

By modifying this general process, one may prepare particles that are hollow or substantially hollow or porous. For example, if the removal of the solvent from the bead is carried out quickly, e.g., by applying a vacuum during the final stage of incubation, porous beads will result.

The particles of the invention can be prepared in any size desired, "Microspheres" may be obtained by nebulizing the polymer solution into a polymer aerosol using either pneumatic or ultrasonic nozzles, such as, for example a Sonotek 8700-60 ms or a Lechler US50 ultrasonic nozzle, each available from Sono[.tek] Corporation, Milton, N.Y., U.S.A. and Lechler GmbH, Metzingen, Germany. Larger particles may be obtained by dispensing the droplets into the non-solvent solution using a syringe or other drop-forming device. Moreover, as will be known to a person of skill in the art, the size of the particle may also be altered or modified by an increase or decrease of the initial concentration of the polymer in the polymer solution, as a higher concentration will lead to an increased sphere diameter.

In an alternative embodiment of the particles described herein, the particles can include a standard and/or a preferred core based on an acrylic polymer or copolymer with a shell of PTFEP. Such particles can provide a preferred spherical shape and improved specific gravity for use in a suspension of contrast media for embolization. The acrylic polymer based polymers with PTFEP shell described herein provide a substantially spherical shape, mechanical flexibility and compressibility, improved specific gravity properties. The core polymers may be formed using any acceptable technique known in the art, such as that described in B. Thanoo et al., "Preparation of Hydrogel Beads from Crosslinked Poly(Methyl Methacrylate) Microspheres by Alkaline Hydrolysis," J. Appl. P. Sci., Vol. 38, 1153-1161 (1990), incorporated herein by reference with respect thereto. Such acrylic-based polymers are preferably formed by polymerizing unhydrolyzed precursors, including, without limitation, methyl acrylate (MA), methyl methacrylate (MMA), ethylmethacrylate (EMA), hexamethyl (HMMA) or hydroxyethyl methacrylate (HEMA), and derivatives, variants or copolymers of such acrylic acid derivatives. Most preferred is MMA. The polymer should be present in the core in a hydrated or partially hydrated (hydrogel) form. Such polymers are preferably cross-linked in order to provide suitable hydrogel properties and structure, such as enhanced non-biodegradability, and to help retain the mechanical stability of the polymer structure by resisting dissolution by water.

Preferably, the core prepolymers are formed by dispersion polymerization that may be of the suspension or emulsion polymerization type. Emulsion polymerization results in substantially spherical particles of about 10 nm to about 10 microns. Suspension polymerization results in similar particles but of larger sizes of about 50 to about 1200 microns.

Suspension polymerization may be initiated with a thermal initiator, which may be solubilized in the aqueous or, more preferably, monomer phase. Suitable initiators for use in the monomer phase composition include benzoyl peroxide, lauroyl peroxide or other similar peroxide-based initiators known or to be developed in the art, with the most preferred initiator being lauroyl peroxide. The initiator is preferably present in an amount of about 0.1 to about 5 percent by weight based on the weight of the monomer, more preferably about 0.3 to about 1 percent by weight based on the weight of the monomer. As noted above, a cross-linking co-monomer is preferred for use in forming the hydrated polymer. Suitable cross-linking co-monomers for use with the acrylic-based principle monomer(s) used in preparing a polymerized particle core, include various glycol-based materials such as ethylene glycol dimethacrylate (EGDMA), diethylene glycol dimethacrylate (DEGDMA) or most preferably, triethylene glycol dimethacrylate (TEGMDA). A chain transfer agent may also be provided if desired. Any suitable MA polymerization chain transfer agent may be used. In the preferred embodiment herein, dodecylmercaptane may be used as a chain transfer agent in amounts acceptable for the particular polymerization reaction.

The aqueous phase composition preferably includes a surfactant/dispersant as well as a complexing agent, and an optional buffer is necessary. Surfactants/dispersants should be compatible with the monomers used herein, including Cyanamer® 370M, polyacrylic acid and partially hydrolyzed polyvinyl alcohol surfactants such as 4/88, 26/88, 40/88. A dispersant should be present in an amount of about 0.1 to about 5 percent by weight based on the amount of water in the dispersion, more preferably about 0.2 to about 1 percent by weight based on the amount of water in the dispersion. An optional buffer solution may be used if needed to maintain adequate pH. A preferred buffer solution includes sodium phosphates ($Na_2HPO_4/NaH_2PO_4$). A suitable complexing agent is ethylene diamine tetraacetic acid (EDTA), which may be added to the aqueous phase in a concentration of from about 10 to about 40 ppm EDTA, and more preferably about 20 to about 30 ppm. It is preferred that in the aqueous phase composition, the monomer to water ratio is about 1:4 to about 1:6.

The polymerization should take place at about ambient conditions, preferably from about 60° C. to about 80° C. with a time to gelation of about one to two hours. Stirring at rates of 100 to 500 rpm is preferred for particle formation, with lower rates applying to larger sized particles and higher rates applying to smaller sized particles.

Once PMMA particles, such as microparticles, are formed, they are preferably subjected to hydrolysis conditions typical of those in the art, including use of about 1-10 molar excess of potassium hydroxide per mol of PMMA. Such potassium hydroxide is provided in a concentration of about 1-15% potassium hydroxide in ethylene glycol. The solution is then heated preferably at temperatures of about 150-185° C. for several hours. Alternatively, to minimize reactant amounts and cost, it is preferred that lesser amounts of potassium hydroxide be used which are less than about 5 molar excess of potassium hydroxide per mole of PMMA, more preferably about 3 molar excess or less. For such hydrolytic reactions, a concentration of about 10-15% potassium hydroxide in ethylene glycol is also preferably used, and more preferably about 14% to about 15%. It will be understood by one skilled in the art, that heating conditions at higher temperatures may be used to decrease overall reaction times. Reaction times may be varied depending on the overall diameter of the resultant particles. For example, the following conditions are able to provide particles having about 35% compressibility and desired stability: for diameters of about 200-300 μm, the solution should be heated for about 7.5 to about 8.5 hours; for diameters of about 300-355 μm, about 9.5 to about 10.5 hours; for diameters of about 355-400 μm, about 11.5 to about 12.5 hours; and for about 400-455 μm, about 13.5 to about 14.5 hours, etc. The particle size can be adjusted using variations in the polymerization process, for example, by varying the stirring speed and the ratio of the monomer to the aqueous phase. Further, smaller sizes can be achieved by increasing surfactant/dispersant ratio.

Following hydrolysis, particles are separated from the reaction mixture and their pH may be adjusted to any range as suited for further processing steps or intended uses. The pH of the particle core may be adjusted in from about 1.0 to about 9.4, preferably about 7.4 if intended for a physiological application. Since size, swelling ratio and elasticity of the hydrogel core material are dependent on pH value, the lower pH values may be used to have beneficial effects during drying to prevent particle agglomeration and/or structural damage. Particles are preferably sieved into different size fractions according to intended use. Drying of particles preferably occurs using any standard drying process, including use of an oven at a temperature of about 40°-80° C. for several hours up to about a day.

To provide desired surface properties to the hydrophilic hydrogel particles, in order to provide adhesion for receiving a PTFEP coating, the surface of the hydrogel may be subjected to treatment with any suitable ionic or non-ionic surfactant, such as tetraalkylammonium salts, polyalcohols and similar materials. A more permanent change in adhesion properties is brought about by rendering the surface of the particles hydrophobic by reaction of its polymethacrylic acid groups with a suitable reactant. Suitable reactants include, but are not limited to, hydrophobic alcohols, amides and carboxylic acid derivatives, more preferably they include halogenated alcohols such as trifluoroethanol. Such surface treatment also prevents delamination of the coating from the core once the coating is applied. Preferred surface treatments may include, without limitation, an initial treatment with thionyl chloride followed by reaction with trifluoroethanol. Alternatively, the surface may be treated by suspending the particles in a mixture of sulfuric acid and a hydrophobic alcohol, such as trifluoroethanol. Such treatments are preferred if the particles are to be coated in that they minimize any delamination of a coating.

Alternatively, and most preferably, the PMA core particles may be coated with a surface layer of and/or infused with barium sulfate. The barium sulfate is radiopaque and aids in visualization of the finished particles when in use. It also provides enhanced fluidization properties to the particles such that it reduces agglomeration especially during drying and allows for fluid bed coating of the PMA particles with an outer coating of PTFEP, thereby providing improved adhesion between a PTFEP outer core and a polymeric acrylate core particles. By allowing fluidization even when the core particles are swollen, barium sulfate also improves the overall coating and adhesion properties. By enabling the coating of the core particles even in a swollen state with PTFEP, barium sulfate also reduces the potential tendency of the PTFEP shells to crack or rupture in comparison with coating the particles in a dry state and then later exposing the particles to a suspension in which the core particles swell and exert force on the shell of PTFEP. A coating of barium sulfate on the core particles is preferably applied by adhesion of the barium sulfate in the form of an opaque coating on the hydrogel surface of the PMA beads. Barium sulfate can further assist in reducing electrostatic effects that limit particle size. By allowing for absorption of additional humidity, the barium sulfate tends to counteract the electrostatic effects.

Barium sulfate crystals adhering only loosely to the PMA particles may be covalently crosslinked or chemically grafted to the particle surface by spraycoating a sufficient amount of an aminosilane adhesion promoter onto the PMA particle. This will help to effectively reduce barium sulfate particulate matter in solution after hydration of the particles.

Exemplary particles include 3-aminopropyl-trimethoxysilane and similar silane-based adhesion promoters.

A further alternative for improving visualization of microparticles made as noted herein include the absorption of a water soluble organic dye inside the hydrogel core particles. Exemplary dyes are preferably those FDA dyes approved for human use and which are known or to be developed for safe, non-toxic use in the body and which are capable of providing acceptable contrast. Organic dyes may include dyes such as D&C Violet no. 2 and others preferably approved for medical device uses, such as for contact lenses and resorbable sutures. Whereas barium sulfate operates as an inorganic filler and finely dispersed pigment that makes the particles visible by light diffraction due to small crystal size, the dyes when impregnated in the particles absorb the complementary part of the visible color spectrum.

Particles, including microparticles made in accordance with the foregoing process for forming a core hydrogel polymer are then coated with PTFEP and/or its derivatives. Any suitable coating process may be used, including solvent fluidized bed and/or spraying techniques. However, preferred results may be achieved using fluidized bed techniques in which the particles pass through an air stream and are coated through spraying while they spin within the air stream. The PTFEP or derivative polymer is provided in dilute solution for spraying to avoid clogging of the nozzle.

Exemplary solvents for use in such solutions include ethyl acetate, acetone, hexafluorbenzene, methyl ethyl ketone and similar solvents and mixtures and combinations thereof, most preferred is ethyl acetate alone or in combination with isoamyl acetate. Typical preferred concentrations include about 0.01 to about 0.3 weight percent PTFEP or its derivative in solution, more preferably about 0.02 to 0.2 weight percent PTFEP, and most preferably about 0.075 to about 0.2 weight percent. It should be understood based on this disclosure that the type of hydrogel core can be varied as can the technique for coating a particle, however it is preferred that a core which is useful in the treatment techniques and applications described herein is formed and subsequently coated with PTFEP and/or its derivatives as described herein.

As previously discussed, the particles can be used in various medical and therapeutic applications, such as embolization, drug delivery, imaging (ultrasound) and as tracer particles. For example, in one embodiment, the invention includes a method of minimizing blood flow to a specific tissue in a mammal. This process, commonly referred to as embolization, includes occluding or obstructing at least a portion of a vessel, or the entire vessel, with one or more of the particles of the invention. Such procedure is particularly useful in the treatment of diseases and pathologies that involve undesirable vascularized tissues, for example, tumor tissue or disorders involving the uncontrolled proliferation of certain cells such as endometriosis. In such procedures, the particle(s) are prepared in accordance with the procedures described above, and may be inserted into the blood vessel by any invasive or non-invasive medical practice known or to be developed in the art such as via a catheter, a syringe, or a surgical incision. The embolization can be carried out such that only a portion of the blood vessel is occluded, or the entire vessel may be occluded. In the method, if desired, one may use particles that have been loaded with an active agent, such as a cytostatic agent, an anti-inflammatory agent, an anti-mitogenic or cell proliferation active agent, a hormone, or any other desirable active agent, as described herein. Embolization particles according to the present invention are capable of demonstrating improved optical visibility, additional radiopacity, and an optimum specific density of about 1.17 g/cm$^3$. The embolization particles in this invention may be used with different dyes as markers as noted above for particle sizes, embedded pharmaceuticals for localized drug delivery and controlled drug elution characteristics.

For use in embolization therapy, particle density is preferably taken into consideration to ensure beneficial properties for particle delivery. Possible clogging of a catheter-based delivery system may occur if using a density-mismatched delivery medium. In addition, it is desirable to include a certain minimum amount of contrast agent in the delivery medium to achieve sufficient levels of fluoroscopic contrast during surgery. Currently, the polymethacrylate hydrogel density is between 1.05 g/cm$^3$ and 1.10 g/cm$^3$ depending on the equilibrium water content. The most common iodinated nonionic contrast agent media with 300 mg iodine per ml have densities of 1.32-1.34 g/cm$^3$. As used herein, "buoyancy" refers to the ability of the particles to be substantially free floating in solution that occurs when the density of the particle is substantially the same as the medium in which it is suspended. Coated particles formed in accordance with the present invention as described herein can reach buoyancy when there is approximately 30% contrast agent in the delivery medium, however, such levels can be adjusted for such preferred use according to techniques described herein.

One method for increasing the density of the particles is by use of heavy water or deuterium oxide ($D_2O$). When heavy water is used to swell the particles, $D_2O$ displaces $H_2O$, thereby increasing the weight of the particles for better dispersion and buoyancy levels. Typically this leads to the ability to add higher amounts of contrast agent of at least about 5% using such a technique. However, some equilibrating effect can occur over time when the particles are contacted with an aqueous solution of contrasting agent. Thus, it is preferred that when using $D_2O$ for this purpose, either that suspension times are kept to a minimum or, more preferably, that the contrast agent be provided in a solution which also uses $D_2O$.

Alternatively, particles of pH 1 can be neutralized with cesium hydroxide and/or the final neutralized particles can be equilibrated with cesium chloride. Such compounds diffuse cesium into the particles, such that either the cesium salt of polymethacrylic acid is formed or polymethacrylic acid is diffused and thereby enriched with cesium chloride.

The cesium increases the density of the particles, thereby increasing the ability to add higher amounts of contrast agent. Typical buoyancy levels can be adjusted using the cesium technique such that about 45 to about 50% contrast agent may be added to the delivery medium as is desired for embolization. Cesium salts are non-toxic and render the particles visible using fluoroscopy. Cesium's atomic weight of 132.9 g/mol is slightly higher than that of iodine providing beneficial effects including increase in overall density and enhancement of X-ray contrast visibility even without a contrast agent. For certain cancer treatments where a radioactive isotope of cesium is desired, such active agent can be used as an alternative cesium source rendering the particles buoyant in an embolic solution as well as able to be used as an active treatment source.

The above-noted techniques for improving density of particles, such as microparticles for embolization or other applications where density and/or buoyancy in solution are applicable properties may be applied in to the preferred particles described herein and/or may be applied for other similar particles. It should be understood that the disclosure is not limited to cesium and/or $D_2O$ treatment of the preferred particles herein and that such techniques may have broader implications in other particles such as other acrylic-based hydrogels and other polymeric particles.

As noted above, barium sulfate may be used between the core particles and the preferred PTFEP coating or introduced into the interior of the core particles using any technique known or to be developed in the art. Also, organic dyes may similarly be included in the particle core. These materials, particularly the barium sulfate, also contribute to an increase in density as well as providing radiopacity. In addition to a general density increase as provided by the above-noted $D_2O$ or cesium compounds, the barium sulfate allows this benefit even upon substantial and/or full hydration, allowing particles in suspension to remain isotonic. Thus, a barium sulfate powder coating can provide an inert precipitate having no effect on physiological osmolarity.

It should be understood, based on this disclosure, that the various buoyancy additives noted above can be used independently or in combination to provide the most beneficial effects for a given core particle and coating combination.

The invention also includes methods of delivering an active agent to a localized area within the body of a mammal. The method includes contacting the localized area with at least one of the particles of the invention as described above, such that an effective amount of the active agent is released locally to the area. Diseases or pathologies that may be treated by this method include any wherein the localized or topical application of the active agent achieves some benefit in contrast to the systemic absorption of the drug. Suitable active agents include NSAIDS, steroids, hormones, nucleic acids, agents used in the treatment of disorders of the gastrointestinal tract, such as, ulcers, Crohn's disease, ulcerative colitis, and irritable bowel syndrome. Other active agents may include tacrolimus, sirolimus, paclitaxel, cis-/carboplatins, antineoplastic agents, doxorubicine and/or receptor blocking agents, e.g., $\alpha v \beta 3$ integrin blockers, which inhibit cell attachment.

If the particle formulated for delivery of an active agent to a localized area is about 1 to about 1,000 μm in diameter, the drug loaded microspheres can be applied to localized areas within the mammalian body using syringes and/or catheters as a delivery device, without causing inadvertent occlusions. For example, using a contrast agent, a catheter can be inserted into the groin artery and its movement monitored until it has reached the area where the localized administration is desired. A dispersion of the particles in a suitable injection medium can be injected through the catheter, guaranteeing only a specific area of the body will be subjected to treatment with drug loaded beads (particles). As will be understood to a person of skill in the art, injection mediums include any pharmaceutically acceptable mediums that are known or to be developed in the art, such as, e.g., saline, PBS or any other suitable physiological medium. In accordance with a further embodiment described herein, the invention includes an injectible dispersion including particles and a contrasting agent which particles are substantially dispersed in the solution. In a preferred embodiment, the particles are also detectible through fluoroscopy.

The polymeric particles of the invention may be used to prepare a sustained release formulation of an active agent for oral administration. The formulation comprises a particle, as described above, loaded with an active agent. The polymeric particle utilized may be hollow, substantially hollow or solid. The particle can be loaded with the active agent either by dispersion or solvation of the active agent in the polymer solution prior to the production of micro-sized particles through spray droplets, pastillation of a polymer melt or carrying out of a cryoextraction process. Alternatively, an unloaded polymer particle can be prepared and subsequently immersed in solutions containing active agents. The particles are then incubated in these solutions for a sufficient amount of time for the active agent to diffuse into the matrix of the polymer. After drying the particles, the active agent will be retained in the polymer particle. If this loading mechanism is utilized, drug loading can be controlled by adjusting drug concentrations of the incubation medium and removing the particles from the incubation medium when an equilibrium condition has been attained.

Moreover, it is envisioned that the active agent can be selected so as to complement the action of the particles in a synergistic fashion, especially if the particles are being used in an occlusive or embolization procedure. For example, if the tissue to which one wishes to minimize blood flow is a tumor tissue, one may wish to load the particles used in the occlusion with a cytostatic drug or an antimitotic drug.

Also provided is a method of tracing the passage of a particle through a blood vessel or other cavity in a mammalian body. The method includes injecting into the vessel, cavity, or a conduit adjacent to such cavity or vessel, at least one tracer particle, wherein the tracer particle is at least a particle prepared in accordance with the procedures described above.

The tracer particle may include a contrast agent that may aid in the visualization of the particle as it passes through the body cavity, blood vessel, and/or other locale. In general, in this application smaller particles are preferred, such as those in the range of about 1 to about 10 μm, especially if the particles are to be injected into the bloodstream. However, the particles may be of any size so long as, for this purpose, they are not large enough to occlude the blood vessel, body cavity, or adjacent cavity or vessel to which the procedure is being applied.

If the particles are loaded with a contrast agent, their movement can be visualized with X-ray machines, or any other contrasting procedure, depending on the contrast agent utilized. However, if the particles do not contain a contrast agent, the flow of the particles may be visualized using $^{19}$F-NMR based computer tomography.

If desired, one may coat the tracer particle containing a contrast agent with a polymer coating. The polymer coating may comprise any polymer known or to be developed in the art, including any phosphazene polymers. If there is any toxicity or concern of toxicity with respect to the contrast agent, it is desirable that the one or more coating is non-biodegradable.

The invention also includes the method of carrying out an enhanced ultrasound imaging procedure (sonography). In order to do this, one must administer to the ultrasound subject at least one hollow microcapsule to the area of the ultrasound subject that one wishes to visualize. Such administration can be accomplished by any means known or to be developed in the art, including by use of a syringe, catheter or other invasive or non-invasive medical device, and/or by a surgical incision. In such method, it is preferable to use particles which are hollow or substantially hollow, i.e. having an inner cavity that is equal to at least about 20%, at least about 30%, at least about 40%, at least about 50%, at least about 80%, at least about 90%, of the volume of the entire particle. The hollow particles are administered to a portion of the ultrasound subject which one wishes to image. While not wishing to be bound by theory, it is speculated that the particles enhance the ultrasound image by increasing the ultrasound "echo" due to their abrupt density change, when compared to the surrounding tissue. The hollow cavities of the particles act to reflect the ultrasound, thereby enhancing the image.

Example 1

Microspheres having a diameter of approximately 500 to 600 μm were prepared. First, a polymer solution was prepared by dissolving PTFEP polymer of a molecular weight $3 \times 10^6$ g/mol in the polymer solvent ethyl acetate to obtain a 2% (wt/v) polymer solution. Four milliliters of this polymer solution was manually dripped into liquid nitrogen using a 5 ml syringe. This dispersion was dispensed onto a frozen layer of 150 milliliters of pentane. (See FIG. 2.) The cryoextraction was allowed to proceed for three days. Subsequently, polymeric particles were retrieved from the reaction vessel, and were air dried at 21° C.

Example 2

Microspheres having a diameter of approximately 350 to 450 μm were prepared. First, a polymer solution was prepared by dissolving PTFEP polymer of a molecular weight $3 \times 10^6$ g/mol in ethyl acetate to obtain a 1% (wt/v) polymer solution. Four milliliters of this polymer solution was manually dripped into liquid nitrogen using a 5 ml syringe. This dispersion was dispensed onto a frozen layer of 150 milliliters of pentane. (See FIG. 2.) The cryoextraction was allowed to proceed for three days. Subsequently, polymeric particles were retrieved from the reaction vessel and were air dried at 21° C.

Example 3

Microspheres having a diameter of approximately 500 to 600 μm were prepared. First, a polymer solution was prepared by dissolving PTFEP polymer of a molecular weight $12 \times 10^6$ g/mol in methylisobutylketone to obtain a 2% (wt/v) polymer solution. Four milliliters of this polymer solution was manually dripped into liquid nitrogen using a 5 ml syringe. This dispersion was dispensed onto a frozen layer of 150 milliliters of a 1:9 (v/v) ethanol/pentane mixture (See FIG. 2.). The cryoextraction was allowed to proceed for three days. Subsequently, polymeric particles were retrieved from the reaction vessel, and dried under reduced pressure at 21° C.

Example 4

Microspheres having a diameter of approximately 500 to 600 μm were prepared. First, a polymer solution was prepared by dissolving PTFEP polymer of a molecular weight $9 \times 10^6$ g/mol in isoamylketone to obtain a 2% (wt/v) polymer solution. Four milliliters of this polymer solution was manually dripped into liquid nitrogen using a 5 ml syringe. This dispersion was dispensed onto a frozen layer of 150 milliliters of pentane. (See FIG. 2.) The cryoextraction was allowed to proceed for three days. Subsequently, polymeric polymers were retrieved from the reaction vessel and dried under reduced pressure at 21° C.

Example 5

Microspheres having a diameter of approximately 500 to 600 μm were prepared. First, a polymer solution was prepared by dissolving PTFEP polymer of a molecular weight $16 \times 10^6$ g/mol in cyclohexanone to obtain a 2% (wt/v) polymer solution. Four milliliters of this polymer solution was manually dropped into liquid nitrogen using a 5 ml syringe. This dispersion was dispensed onto a frozen layer of 150 milliliters of a 1:1 (v/v) ethanol/diethyl ether mixture. (See FIG. 2.) The cryoextraction was allowed to proceed for three days. Subsequently, polymeric particles were retrieved from the reaction vessel and dried under reduced pressure at 21° C.

Example 6

Microspheres having a diameter of approximately 500 to 600 μm were prepared. First, a polymer solution was prepared by dissolving PTFEP polymer of a molecular weight $3 \times 10^6$ g/mol in ethyl acetate to obtain a 2% (wt/v) polymer solution. Four milliliters of this polymer solution was manually dripped into liquid nitrogen using a 5 ml syringe. This dispersion was dispensed onto a frozen layer of 150 milliliters of hexane. (See FIG. 2.) The cryoextraction was allowed to proceed for three days. Subsequently, polymeric particles were retrieved from the reaction vessel and air dried at 21° C.

Example 7

Microspheres having a diameter of approximately 500 to 600 μm were prepared. First, a polymer solution was prepared by dissolving PTFEP polymer of a molecular weight $3 \times 10^6$ g/mol in ethyl acetate to obtain a 2% (wt/v) polymer solution. Four milliliters of this polymer solution was manually dripped into liquid nitrogen using a 5 ml syringe. This dispersion was dispensed onto a frozen layer of 150 milliliters of ethanol. (See FIG. 2.) The cryoextraction was allowed to proceed for three days. Subsequently, polymeric particles were retrieved from the reaction vessel and air dried at 21° C. The particles were noticeably gel-like and after drying were ellipsoid in shape.

Example 8

Microspheres having a diameter of approximately 500 to 600 μm were prepared. First, a polymer solution was prepared by dissolving PTFEP polymer of a molecular weight $3 \times 10^6$ g/mol in ethyl acetate to obtain a 2% (wt/v) polymer solution. Four milliliters of this polymer solution was manually dripped into liquid nitrogen using a 5 ml syringe. This dispersion was dispensed onto a frozen layer of 150 milliliters of diethylether. (See FIG. 2.) The cryoextraction was allowed to proceed for three days. Subsequently, polymeric particles were retrieved from the reaction vessel and air dried at 21° C. The resultant particles were, after drying, compact and uniformly spherical.

Example 9

Figure 6:
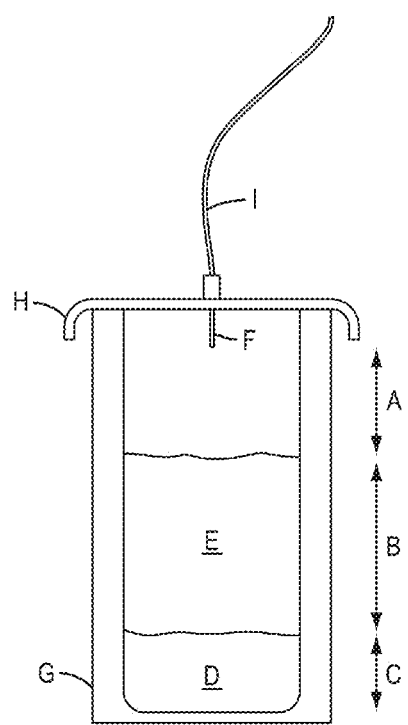

A two liter cryovessel as shown in FIG. 6 was filled with 100 milliliters of diethyl ether as a non-solvent. The cryovessel had the features and typical dimension as shown below in Table 1.

TABLE 1

| | Legend | Typical Dimensions |
|---|---|---|
| A | Drop Distance Length | 5-10 cm |
| B | Liquid Nitrogen Layer Depth | 5-10 cm |
| C | Nonsolvent Layer Depth | 1-2 cm |

TABLE 1-continued

| Legend | | Typical Dimensions |
|---|---|---|
| D | Nonsolvent | — |
| E | Solvent | — |
| F | Syringe Needle Tip | 25 G-33 G |
| G | Dewar | 1-2 l volume |
| H | Lid | — |
| I | Teflon Tubing | 0.8 mm diameter; 40 cm length |

Liquid nitrogen was slowly added until the non-solvent froze. The vessel was then filled with additional liquid nitrogen, until the amount of liquid nitrogen rose approximately 5 to 10 cm when measured vertically above the non-solvent layer. The vessel was closed with an insulated lid, and a syringe needle connected via Teflon tubing to a syringe pump was inserted through a small opening in the lid.

Figure 7:
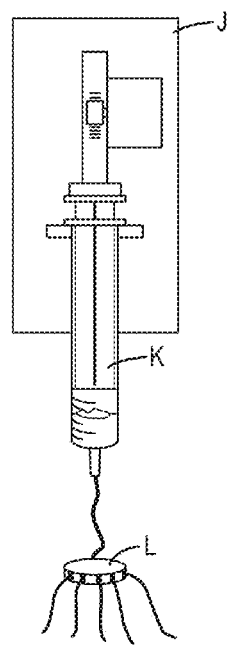

The syringe pump as shown in FIG. 7, was used to dispense between 5 to 15 milliliters of the 5 to 40 mg/ml polymer solution in ethyl acetate, slowly into the cryovessel. The syringe pump had the following features: a pump housing (J), a syringe (K) and a Teflon® distributor with Teflon® tubing attached (L). The rate of the pump was adjusted to approximately 10 milliliters dispensing volume per hour. A Teflon® cylinder with one inlet and one to eight outlets is used to distribute the dispensed volumes into several vessels in parallel. (It is preferable that the ratio of solvent to non-solvent volume stays below 10% (v/v). Otherwise the particles may adhere to one another.) After the polymer solution was completely dispensed into the vessel, another 100 milliliters of non-solvent was slowly poured on top of the liquid nitrogen.

In carrying out this process, it is noted that it is preferable that the needle tips used for dispensing are small, such as the G33 size. Additionally, the dropping distance should be more than 5 cm, so that the droplets aided by gravity immediately sink into the liquid nitrogen upon hitting the surface.

The liquid nitrogen in the vessel was slowly allowed to evaporate, taking approximately one day. The non-solvent slowly began to melt, and the polymer solution droplets, still frozen, sank into the cold non-solvent. After another day of incubation, the now gelled polymer beads (particles) were retrieved from the vessel by simple filtration. They were allowed to dry at room temperature for approximately 30 minutes and then were ready for use in any of the applications described herein.

Example 10

Figure 3A:
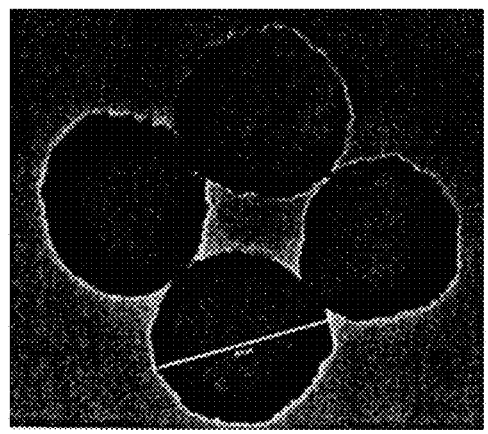
FIG. 3A and FIG. 3B show unloaded polyphosphazene particles (microspheres) as prepared by one embodiment of the cryoextraction method as described herein.
Figure 3B:
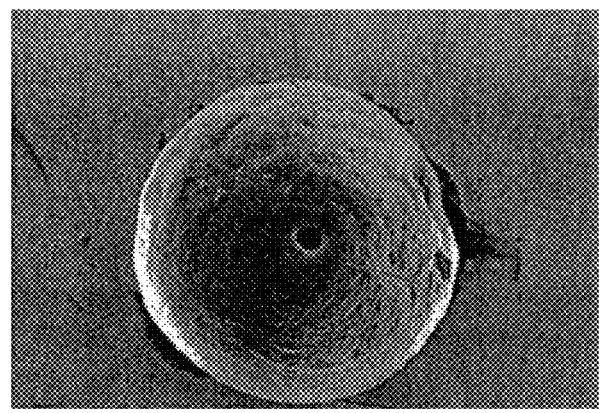

The microspheres prepared by the process of Example 1 were examined for shape and surface morphology by optical microscope, scanning electron microscope (SEM) and atomic force microscopy. The results of these analyses are shown in FIGS. 3A and 3B). FIG. 3A shows the microspheres as they appear using an optical microscope at 4× magnification. FIG. 3B shows a microsphere as it appears using a scanning electron microscope at 100× magnification.

It can be seen that surface morphology of the unloaded spheres is typical for semi-crystalline polymers above glass transition temperature. Amorphous as well crystalline regions are prevalent throughout the sample surface. The surface is microporous in nature, with pore sizes ranging from nanometers to few micrometers in diameter.

Figure 4A:
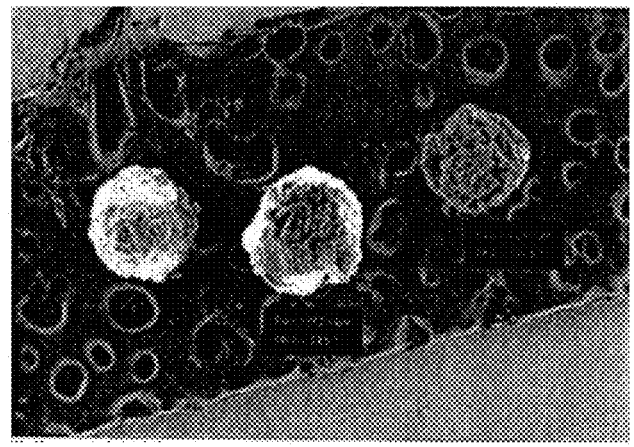
FIGS. 4A and 4B show a particle (microsphere) formed according to one embodiment of the invention loaded with bovine insulin (20% (wt/wt)) at 100× magnification SEM.
Figure 4B:
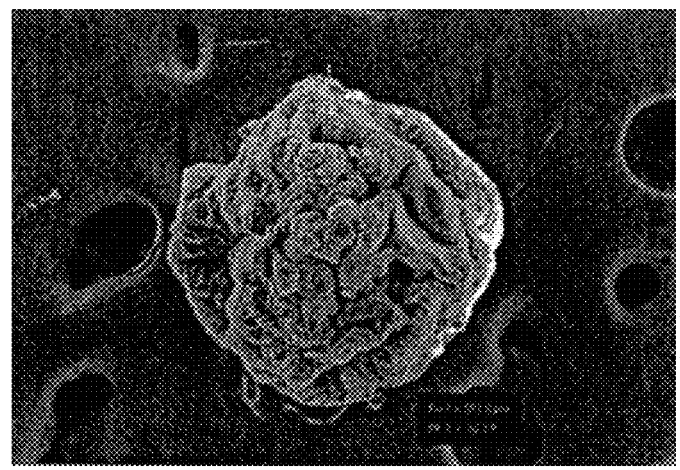
Figure 5A:
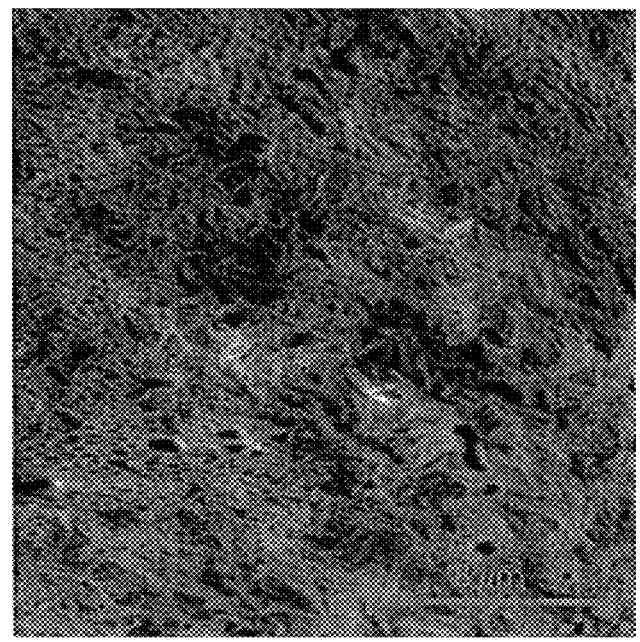
FIG. 5A and FIG. 5B show the surface morphology of unloaded polyphosphazene microspheres.
Figure 5B:
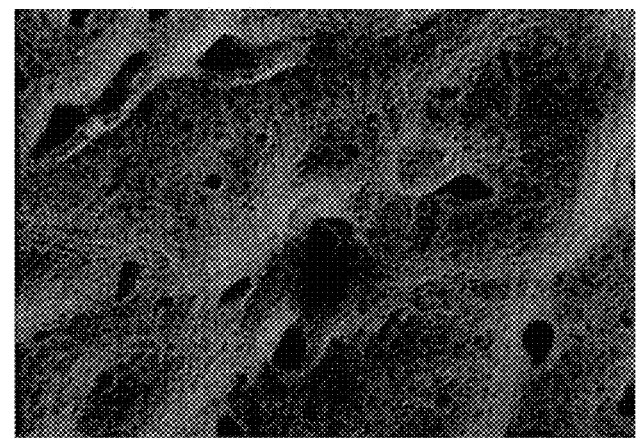

Particles loaded with bovine insulin were also analyzed using scanning electron microscopy (100× magnification). The result of these analyses can be seen in FIG. 4A and FIG. 4B).

Example 11

Several polymerizations were carried out using varying combinations of PMMA and three different crosslinking monomers (EDGMA, DEGDMA and TEGDMA), different radical initiators (benzoyl peroxide (BPO) and lauroyl peroxide (LPO), EDTA as a complexing agent and varying dispersants (Cyanamer 370M, polyacrylic acid (PAA) and varying types of polyvinyl alcohol (PVA) to achieve the preferred core particles. In some polymerizations, sodium phosphate buffer solution ($Na_2HPO_4/NaH_2PO_4$) was used. It was observed that some of the reaction procedures went unsuccessful due to the type of dispersant and concentration chosen. Failure of the dispersant was demonstrated in the form of early onset of an exothermic reaction, coalescing aqueous and organic phases and premature onset of the vitrification phase. Only the successful examples are shown. The successful runs are shown below in Table 2, which includes the components, concentrations and reaction conditions for such samples (1-6).

TABLE 2

| Sample | 1 | 2 | 3 | 4 | 5 | 6 |
|---|---|---|---|---|---|---|
| Monomer | PMMA 99.0 g | PMMA 190.0 g | PMMA 182.0 g | PMMA 200.2 g | PMMA 200.2 g | PMMA 200.2 g |
| Crosslinker | EDGMA (1 wt %/ monomer) | EDGMA (1 wt %/ monomer) | EDGMA (1 wt %/ monomer) | DEGDMA (0.5 mol %/ monomer) | TEGDMA (0.5 mol %/ monomer) | TEGDMA (0.5 mol %/ monomer 7.5 mMol DDM) |
| Radical Initiator | LPO (0.3 wt % monomer) | LPO (0.3 wt % monomer) | LPO (0.3 wt % monomer) | LPO (0.3 wt % monomer) | LPO (0.3 wt % monomer) | LPO (0.3 wt % monomer) |
| Complexing Agent | EDTA 22 mg | EDTA 44 mg | EDTA 44 mg | EDTA 56 mg | EDTA 56 mg | EDTA 56 mg |
| Monomer/ Water Ratio | 1:5 | 1:5 | 1:5 | 1:6 | 1:6 | 1:6 |
| Dispersant | PVA 4/88 35% PVA 26/88 65% 1 wt %/ water | PVA 4/88 35% PVA 26/88 65% 0.5 wt %/ water | PVA 26/88 0.25 wt %/ water | PVA 26/88 0.23 wt %/ water | PVA 26/88 0.23 wt %/ water | PVA 26/88 0.23 wt %/ water |

TABLE 2-continued

| Sample | 1 | 2 | 3 | 4 | 5 | 6 |
|---|---|---|---|---|---|---|
| Buffer Solution | No | No | No | Yes | Yes | Yes |
| Reaction Temperature/ Time | 1 h 67° C. 2 h 70° C. 1 h 80° C. | 1 h 67° C. 2 h 70° C. 1 h 80° C. | 1 h 67° C. 2 h 70° C. 1 h 80° C. | 1 h 67° C. 2 h 70° C. 1 h 80° C. | 1 h 67° C. 2 h 70° C. 1 h 80° C. | 1 h 67° C. 2 h 70° C. 1 h 80° C. |
| Outcome (particle size) | 1-50 μm due to dispersant conc. | 20-200 μm due to dispersant conc. | 100-200 μm due to dispersant conc. | 1-100 μm due to initial stirring at 400 rpm | 1-100 μm due to initial stirring at 400 rpm | 50-1,000 μm due to initial stirring at 130 rpm |

Example 12

Hydrogel microparticles formed in accordance with the procedures described herein were evaluated for buoyancy and suspension properties for use in embolization applications. The microparticles included a sample using unmodified polymethacrylic acid potassium salt hydrogel particles (Sample A); a sample using trifluoroethyl esterified polymethacrylic acid potassium salt hydrogels (Sample B); and a sample using the same hydrogel as Sample B, but wherein the particles were coated with PTFEP (Sample C). An isotonic phosphate buffered saline solution of pH 7.4 having 0.05 volume % Tween™ 20 was prepared by dissolving 5 phosphate buffered saline tablets (Fluka®) in 999.5 ml of milliQ ultrapure water. 0.5 ml of Tween 20™ surfactant was added to the solution. Solutions having between 20 and 50 percent by volume of Imeron300® contrast agent in the isotonic buffered saline solution were then prepared for evaluation.

The contrast agent solutions that were prepared were then placed in 4 ml vials in aliquots of 2 ml each. To the vials, 50-80 mg of the hydrated hydrogel Samples A-C were added. Each Sample was first hydrated by adding to 100 mg of dry hydrogel microparticles either 900 mg of isotonic phosphate buffered saline solution or $D_2O$ to obtain 1 ml swollen hydrogel. Buoyancy properties were measured immediately and every 10 minutes thereafter until buoyancy equilibrium was achieved and/or surpassed.

All of the particles reached equilibrium density in the contrast agent solution having 30-40% contrasting agent within 5 min. Particles which were swollen with $D_2O$ were heavier within the first 10 minutes, but the $D_2O$ did diffuse out of the particles over time within 15-20 min. of immersion. If additional water which could displace the $D_2O$ were not added, microparticles hydrated with $D_2O$ would be able to increase the contrast agent percentage achievable with adequate buoyancy by as much as 5%. Particles began to float to the top over time when the contrast agent was added in percentages of 40%-50%.

The equilibrium buoyancy (matching densities) was achieved for Sample C in 31±1 volume percent of contrast agent in solution. With regard to Samples A and B, swelling behavior and subsequent density are typically dependent on crosslinking content, pH, ionic strength and valence of cations used. However, it was assumed herein that the swelling does not influence buoyancy due to the sponge-like nature of the polymethacrylic acid hydrogel material. After such material was coated with the PTFEP as in Sample C, a time lag of swelling was observed and buoyancy equilibrium was slower to achieve.

Example 13

In order to take account of the time lag and to achieve a more preferred density, as well as to enhance the fluoroscopic visibility of the particles, cesium treatment was then effected for the types of microparticles used in Samples B and C of Example 12.

100 mg of Sample C and of Sample B were hydrated each for 10 min. in a 30 weight percent solution of sodium chloride. The supernatant liquid was decanted after equilibrium and the microparticles were washed thoroughly with deionized water. They were then equilibrated for another 10 min., decanted and suspended in 3 ml of surfactant-free isotonic phosphate buffer solution at a pH 7.4. The effect on buoyancy was then evaluated using contrast agent solutions varying from 20 to 50% by volume of Imeron® 300. In this Example, 0.1 g of the microparticles of Samples B and C were used. 3.5 ml of Imeron 300 contrast agent were provided to the initial buffer solution which included 4.0 ml isotonic phosphate buffer/Tween™ 20 solution.

The equilibration procedure using cesium chloride yielded particles of increased density. Both microparticle samples showed a final buoyancy in the Imeron® 300 contrast agent solutions at concentrations of 45-50% contrast agent, regardless of the presence or absence of Tween™ 20 surfactant. The conditions for saturation appeared to be dependent upon the initial pH of the particles, the pH used during the procedure and the corresponding saturation with methacrylic acid groups in the particle. At pH below 3.6, constant exchange between protons and cations was observed. As a result, more beneficial results were shown at pH above about 3.6 and below about 6.6 to temper the amount of cesium. Within the preferred range, buoyancy can be varied. At reasonably neutral levels, based on test at pH of 7.4, the microparticles did not lose their buoyancy after storage in the contrast agent buffered solution over night.

Example 14

Figure 8:
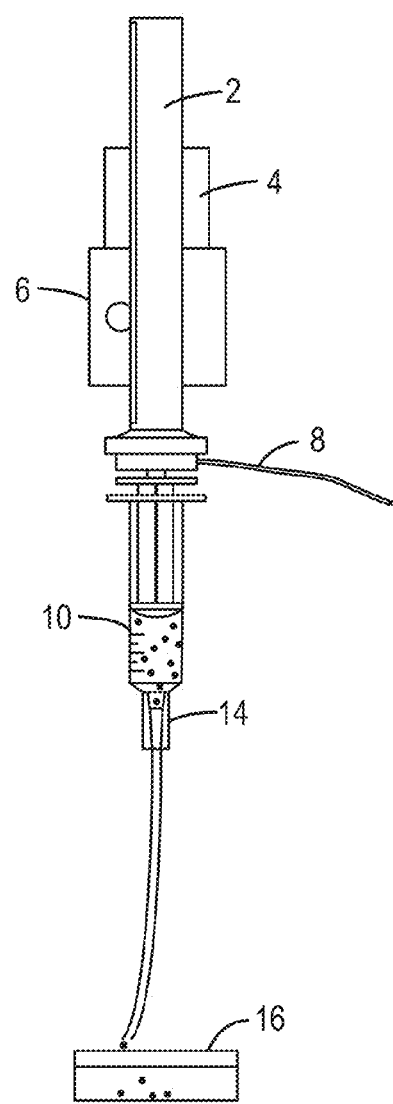
FIG. 8 is a cross-sectional view of an apparatus for use in microcatheter testing of microparticles in Example 14 herein.

Further compressibility and mechanical property testing were done on microspheres in accordance of Samples B and/or C of Example 12. A pressure test stand which was used for further evaluation is shown in FIG. 8. An automated syringe plunger 2 having a motor 4 for providing a variable feed rate of 0 to 250 mm/h and a gear box 6 was further equipped with a Lorenz pressure transducer 8 capable of measuring forces in the 0 to 500 N range. The syringe plunger 2 was in communication with a syringe body 10 as shown. The digital output of the transducer was recorded using a personal computer. The syringe body 10 was filled with 5 ml of a solution of contrast agent in isotonic phosphate buffer/surfactant (Tween™ 20) solution in a concentration of about 30-32 volume percent contrast agent. Microparticles were provided to the syringe as well in an amount of 56 mg dry mass. The syringe contents were then injected through the microcatheter 12 which was attached to the distal end 14 of the syringe. The microcatheter had a lumen diameter of 533 μm. The force needed to push the microparticles through the catheter into the Petri dish 16 (shown for receiving microparticle solution) was measured and recorded as pressure.

In order to make certain calculations, the following information was applied as based on typical use of microspheres for embolization. Typically such microspheres have a water content of about 90% such that a vial for embolization would therefore contain 0.2 mg of embolization particles in 9.8 ml of injection liquid (2 ml of hydrated microparticles in 8 ml supernatant liquid). Standard preparation procedures include adding 8 ml of Imeron® 300 contrast agent to the contents of a single vial. This would provide an equilibrium concentration of contrast agent of 8 ml/(9.8 ml+8 ml)=44.9 volume percent within an injection solution. The solution is typically drawn up in 1 ml syringes for final delivery. The injection density thus equals:

$$\rho = V_{Emb}/V_{Tot} = 2 \text{ ml}/18 \text{ ml} = 0.111 \text{ Embolization agent per volume fraction.}$$

The Sample C spheres demonstrated approximately the same equilibrium water content as typical embolization spheres. To achieve the same injection density desired for typical surgical procedures, 56 mg of Sample C microspheres were added to 5 ml of a 31 volume percent contrast agent solution in isotonic phosphate buffer and surfactant as noted above.

The Sample B and C microspheres were evaluated in different microcatheters of equal lumen diameter at a pH of 7.4. Injections in both the horizontal and vertical direction were made under different buoyancy levels and using different swelling levels (based on pH of 6.0 in contrast to pH 7.4). The results demonstrated that as long as the diameter of the microspheres was below the internal diameter of the microcatheter, the microparticles passed through the catheter without additional frictional force in the same manner as the reference solution. An increase to about 1.0 to 1.4 kg gravitation force was measured when the microparticle diameter reached the same dimension as the lumen diameter. At roughly 20% compression, forces of about 1.5-2.3 kg were needed to overcome frictional forces within the catheter. Forces greater than 5 kg were taken as a guideline for moderate to high injection pressures. When particles are heavier than the injection medium, clogging was observed when injecting in the vertical position. When injecting the microparticles in the horizontal position, it was observed that serious clogging was alleviated and that larger volumes were injectible over time.

Injection pressure was further minimized when a lower pH (reduced swelling) was used in combination with horizontal injection such that the injection pressures were comparable to the injection media itself. In addition, injection of Sample C microparticles also exhibited a good injection pressure pattern at a physiological pH. The catheter entrance did not clog and each peak in the curve corresponded to either a single microparticle or number of particles passing through the catheter.

The results of the various catheter simulation tests shows that the invention can be used to form injectible microparticles having a density which substantially matches the density of the injection medium for embolization use. The particles' compressibility can further be such that it can be injected without forces over more than about 5 kg on the syringe plunger. The pH of the injection medium can be taken down to about 6 or injections can be done horizontally to increase the ease of passage of Sample B and C microparticles through the catheter. Once within the blood stream, the particles can expand to their original size in the pH 7.4 environment.

Additional swelling tests were conducted on the microparticles of Sample C and it was observed that when ion concentrations were low, swelling increased. In higher concentrated solutions, swelling decreased. Continued dilution of the microparticles of Sample C in a buffer solution led to an increase from 17% to 20% in size of the microparticles. When mixed into an isotonic phosphate buffer solution, the microparticles initially increase in size between 83.8 and 97%, wherein in deionized water, size increases are from about 116.2 to about 136.6%, referring to the dry particles.

In further testing to evaluate the compressibility of the microparticles of Sample C, the syringe pressure test stand of FIG. 8 was used, however, an optical microscope was used to evaluate the microparticles as they passed through a progressively narrowed pipette which was attached to polyethylene tubing connected to the syringe containing a phosphate buffer solution suspension of microparticles of Sample C. The pipette narrowed to an inner diameter of 490 μm and the pipette was mounted to a Petri dish such that the narrowest part was submerged in phosphate buffer solution to avoid optical distortion and to collect the liquid ejected from the pipette during measurement. Optical microscope pictures were taken of the microparticles passing through the pipette before and during compression. In observing the microparticles, none of them underwent a fracture, nor did they form debris or coating delamination after passing through the narrow site. Microparticles which were chosen to be deliberately too big for the narrow site (for a compression of about 40%) did not break or rupture, but clogged the narrow site instead. The maximum compressibility under a reasonable amount of force on the microparticles while still allowing the microparticles to pass through the catheter was about 38.7%. Based on these evaluations, the microparticles according to Sample C demonstrate properties that would allow particles which are too large to clog the catheter rather than break up and cause potential damage to the patient. The test results provided suggested preferred use parameters for Sample C microparticles for embolization use as shown in Table 3 below:

TABLE 3

| Particle Radius (μm) | Constriction (μm) | Compression (%) | Force Needed (kg) |
|---|---|---|---|
| 340 | 540 | 25.9 and 26.5 | 2.58 and 1.92 |
| 360 | 540 | 33.3 | 3.19 |
| 330 | 540 | 22.2 | 2.83 |
| 330 | 540 | 22.2 | 2.14 |
| 370 | 540 | 37.0 and 37.3 | 3.59 and 2.77 |
| 330 | 540 | 22.2 | 2.08 |
| 320 | 540 | 18.5 and 18.4 | 1.61 and 1.38 |
| 330 | 540 | 22.2 | 1.71 |

Figure 9A:
FIGS. 9A and 9B show an SEM at 1.0K× magnification of the surface of the Sample C microparticles just after the hydration/dehydration cycle and at a 50.00K× magnification of the film thickness of microparticles formed in accordance with Sample C of Example 12 used in the evaluation of Example 14, respectively.
Figure 9B:
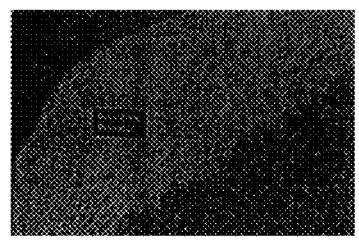
Figure 10A:
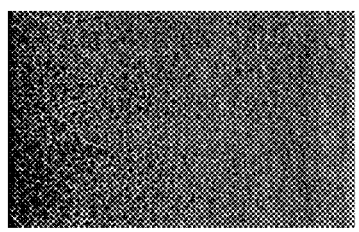
FIGS. 10A, 10B, 10C and 10D are SEMs of microparticles made in accordance with Sample C of Example 12 used in the evaluation of Example 14 after passing through a catheter showing surface features (FIGS. 10A, 10B and 10C) at 1.0K× magnification and at 5.0K× magnification (FIG. 10D)
Figure 10B:
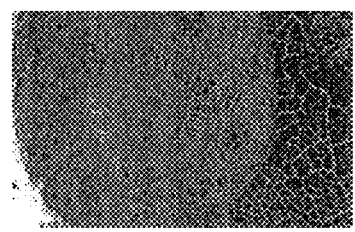
Figure 10C:
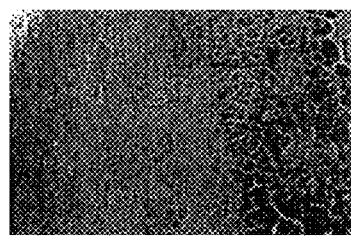
Figure 10D:
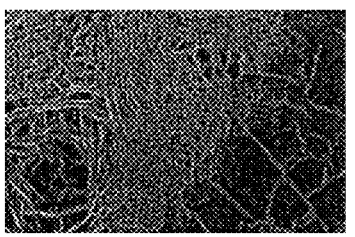

Sample C microparticles were further subjected to mechanical and thermal stress stability testing. Microparticles, after passing through a Terumo Progreat Tracker catheter were washed with deionized water to remove residual buffer solution along with contrast agent. They were dehydrated for 12 h at 60° C. and then transferred to an SEM for surface analysis. They were compared with particles from the original batch of microparticles which had undergone the same hydration/dehydration cycle in milliQ ultrapure water, but which had not been passed through the catheter. FIGS. 9A and 9B show the surface of the Sample C microparticles just after the hydration/dehydration cycle and the film thickness of an exemplary Sample C microparticle, respectively. SEMs after passing through a catheter at various magnifications (FIGS. 10A, 10B, 10C and 10D) show that the coating did not delaminate (FIG. 10A). Some microparticles did demonstrate some stretching out in the coating film (FIGS. 10B and 10C). However, a closer magnification as in FIG. 10D demonstrates that the morphology of the coating layer is still intact.

Figure 11A:
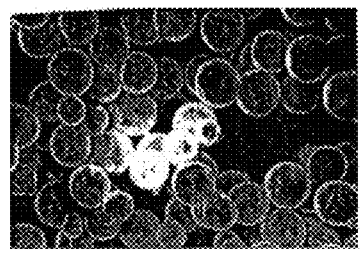
FIGS. 11A, 11B, 11C and 11D are SEMs of microparticles formed in accordance with Sample C of Example 12 after thermal stress testing in Example 14.
Figure 11B:
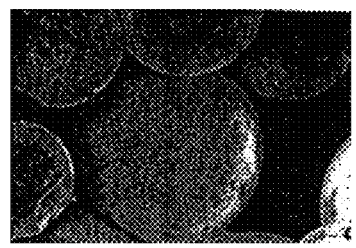
Figure 11C:
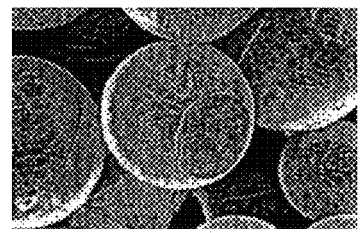
Figure 11D:
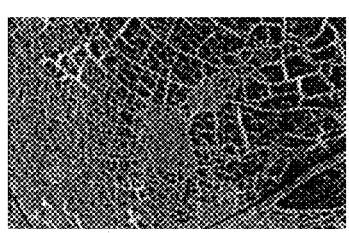

A sterilizer was filled with 2 l of deionized water and 10 vials each having 56 mg of Sample C microparticles in 3.3 g of solution of isotonic phosphate buffer/surfactant (Tween™ 20) and turned on. The water boiling point was reached about 15 min. after the start of the sterilizer, and temperature was held at that point for 3 min. to remove air by water vapor. The vessel was then sealed shut to raise pressure and temperature to 125° C. and 1.2 bar pressure. This took approximately 10 min. The temperature was then maintained for 15 min, and then the vessel was shut down for a cooling phase. A temperature of 60° C. was reached about 30 min later, after which the vessel was vented, the samples withdrawn and the vessel shut tightly. A sample vial was opened, and the supernatant liquid decanted. The microparticles were washed with deionized water. After dehydration, they were subjected to measurement using an SEM. The results demonstrated only a small number of delaminated coatings on the microparticles under such thermal stress (see FIG. 11A in the strong white contrast portion). The overall percentage of such microparticles was only about 5 to 10%. Close up, the film delamination which did occur appears to have occurred along crystalline-amorphous domain boundaries in the PTFEP coating (see FIG. 11B). Most of the microparticles showed only minor defects (such as a minor circular patch being missing), but no damage to the hull of the microparticles (see FIGS. 11C and 11D).

Example 15

Microparticles were formed in accordance with a preferred embodiment herein. A deionized water solution of polyvinyl alcohol (PVA) was prepared using about 23 g of PVA of weight average molecular weight of about 85,000-124,000, which PVA was about 87-89% hydrolyzed and 1000 g water. A phosphate buffer solution was prepared using 900 g deionized water, 4.53 g disodium hydrogen phosphate, 0.26 g sodium dihydrogen phosphate and 0.056 g ethylenediamine tetraacetic acid (EDTA). Methyl methacrylate (MMA) monomer was vacuum distilled prior to use.

Polymerization was carried out in a three-necked, round-bottomed, 2000-ml flask with a KPG mechanical stirring apparatus attached. The flask was also equipped with a thermometer, reflux condenser and a pressure release valve with a nitrogen inlet. The polymerization process further utilized 100 ml of the PVA solution prepared above, 900 ml of the phosphate buffer solution, 0.65 g of dilauroyl peroxide, 200.2 g methacrylic acid methyl ester and 2.86 g triethylene glycol dimethacrylate.

The PVA and buffer solutions were provided to the reactor flask. The distilled MMA and triethylene glycol dimethacrylate were introduced, dilauroyl peroxide then added to the same flask and the components were agitated to ensure dissolved solids. The reaction flask was flushed with argon and the stirrer speed set to at 150 rpm to produce particle sizes of a majority in the range of 300-355 µm. Stirring continued for approximate 5 minutes. The stirrer was then set to 100 rpm and argon flushing was discontinued. The reaction flask was then subjected to a water bath which was heated to 70° C. and held at approximately that temperature for about 2 hours. The temperature of the bath was then increased to 73° C. and held for an hour, then the water bath temperature was raised again to 85° C. and held for another hour. The stirring and heat were discontinued. The solution was filtered and the resulting polymethylacrylate microparticles were dried in an oven at 70° C. for about 12 hours. The microparticles were subjected to sieving and collected in size fractions of from 100-150; 150-200; 200-250; 250-300; 300-355; 355-400; and 400-450 µm with a maximum yield at 300-355 µm.

The PMMA microparticles thus formed were then hydrolyzed. A portion of 100 g 250-300 µm sized microparticles, 150 g potassium hydroxide and 1400 g of ethylene glycol were added to a 2000 ml flask, reflux condenser with drying tube connected, and the mixture was heated at 165° C. for 8 hours for full hydrolysis. The mixture was allowed to cool to room temperature, solution decanted and the microparticles were washed with deionized water. The procedure was repeated for other calibrated sizes of microparticles (the following reaction times applied: 300-355 micron particles: 10 hours; 355-400 micron particles: 12 hours and 400-455 micron particles: 14 hours).

The microparticles were finally acidified with hydrochloric acid to a pH of 7.4, and dried in an oven at approximately 70° C.

Example 16

Microparticles formed in accordance with Example 15 were then esterified in this Example. For esterification surface treatment, 800 g of dried microparticles from Example 15 were weighed in a 2 L reaction vessel with a reflux condenser. 250 g thionyl chloride in 1.5 L diethyl ether were added under stirring. Stirring was continued at room temperature for 20 hours. The solvent and volatile reactants were removed by filtration and subsequent vacuum drying. Then 500 g trifluoroethanol in 1.5 L ether were introduced and the suspension stirred for another 20 hours at room temperature. The particles were finally dried under vacuum.

Example 17

In an alternative surface treatment to Example 16, 800 g dried microparticles from Example 15 were reacted with 1140 g trifluoroethanol and 44 g sulfuric acid added as a catalyst. The mixture was stirred for 20 hours at room temperature, filtered and dried under vacuum.

Example 18

800 g of dry PMMA potassium salt microparticles which were partially esterified with trifluoroethanol as described above in Examples 15-16 were spray coated with PTFEP in an MP-1 Precision Coater™ fluidized bed coating apparatus (available from Aeromatic-Fielder AG, Bubendor, Switzerland). The particles were picked up by an air stream (40-60 m$^3$/h, 55° C. incoming temperature) and spray coated with PTFEP solution microdroplets from an air-fluid coaxial nozzle. The solution composition was 0.835 g PTFEP, 550 g ethyl acetate and 450 g isopentyl acetate. It was fed through the nozzle's 1.3 mm wide inner bore at a rate of 10-30 g/min. At the nozzle head, it was atomized with pressurized air (2.5 bar). The total amount of spray solution (3 kg) was calculated to coat the particle with a 150 nm thick PTFEP film.

Example 19

The dry potassium salt microparticles of Examples 15-16, which were partially esterified with trifluoroethanol as described above, were spray-coated with diluted PTFEP solution in ethyl acetate in a commercially available fluidized bed coating device (see Example 16). 100 mg of such coated, dried microparticles as well as 100 mg of uncoated, dried PMA potassium salt microparticles which were partially esterified with trifluoroethanol, were immersed in about 30% aqueous cesium chloride solution, prepared by dissolving 30.0 g cesium chloride in 100 ml deionized water. The supernatant liquid was decanted after 10 min. equilibrium time and the microparticles were washed thoroughly with deionized water, equilibrated for another 10 min., decanted and suspended in 3 ml surfactant free phosphate buffer solution at a pH of 7.4. Density of the particles in solution was measured for matching density in a contrast agent solution. To each type of microparticle was added a contrast agent solution which included a ratio of 3.5 ml of Imeron® 300 contrast agent (density 1.335 g/ml) and 4 ml phosphate buffered saline (density 1.009 g/ml). Both hydrogel types reached buoyancy at levels of 45-50% contrast agent in solution. This corresponds to an increased density of the microparticles of 1.16 g/ml.

Example 20

Microparticles were formed in accordance with the procedure of Example 15 with the exception that an exterior barium sulfate coating was prepared on the microparticles after neutralization of the particles and the microparticles were not dried after neutralization prior to the barium sulfate coating step. To prepare the barium sulfate coating, 2500 ml hydrated particles were subjected to 2000 ml of 0.5 M sodium sulfate ($Na_2SO_4$) solution and saturated for 4-12 hours. To the particle suspension was then slowly added 1950 ml of 0.5 M barium chloride ($BaCl_2$) solution under stirring at room temperature. After washing with excess deionized water, the resulting particles in a swollen state included a barium sulfate powder coated surface. The particles were then dried and esterified in the manner noted above in Example 16. The particles were then coated using the fluidized bed process of Example 21 below. The resulting microparticles were externally coated with a non-adhesive barium sulfate powder. Barium sulfate coatings prepared in accordance with this invention and procedure are capable of preventing particle agglomeration during drying and also increase density. The concentration and ratios of barium sulfate may be varied to provide different results and a use of an excess of sodium sulfate can minimize residual barium chloride. The particles formed in accordance with this example were effectively washed with hot water to minimize excess barium sulfate powder that may contaminate vials, etc. The barium sulfate works effectively to prevent adhesion of particles prior to drying to assist in fluidization of the hydrated microparticles.

Example 21

Fluidized bed coating of barium sulfate powdered beads was performed using polymethacrylate beads with a surface layer of barium sulfate famed in accordance with Example 20 but an excess of barium chloride was used such that barium ions diffused inside the core and formed a precipitate inside the hydrogel core.

In preparing the particles, the same procedure for barium sulfate coated particles set forth in Example 20 was repeated with the exception that the order of addition was reversed. Thus, 2500 ml hydrated microparticles were suspended in 2500 ml deionized water and slowly, 5 mol % (200 ml) of a 0.5 M ($BaCl_2$) were added slowly under stirring. The addition was performed within a time period of three minutes to prevent irreversible barium acrylate formation taking place. The suspension was then immediately quenched with the double amount (400 ml) of 0.5 M sodium sulfate ($Na_2SO_4$) solution under stirring at room temperature. Afterwards, the particles were washed three times with 2 L of deionized water each. This procedure precipitated barium sulfate inside the particles.

The resulting precipitate was precipitated within the pores of the hydrogel core and could not be removed by multiple washings with water. The particles thus formed were found to have a permanent increased density in contrast to unmodified particles. The density increase was controllable by the molar amount of barium chloride used. Amounts ranging from 0-15 mol % of barium chloride were used reproducibly with this procedure. It was observed during evaluations of this procedure that, if the time period of addition exceeded 5 minutes, based upon the diffusion speed of barium chloride within the particles, the outer pores of the hydrogel core became irreversibly crosslinked, thereby preventing the barium sulfate precipitate inside from leaching out. This effect was visible by optical microscopy as the “diffusion front” of the barium sulfate was clearly visible as a white band inside the particle, whereas the surface remained clear.

Both Examples 20 and 21 provided particles having anti-adhesive properties that tend not to agglomerate during drying processes; therefore avoiding surface damage. Generally, such an advantage helps minimize the amount of particles needed for a fluidized bed procedure as the particles can be fluidized without being completely dried. The residual water content may be increased up to 1:1 based on dry weight without agglomeration. The Examples also produce particles with increased density properties wherein the density change appears to be permanent.

It should also be understood according to this disclosure that generally when applying the procedures noted herein, barium sulfate may be introduced in accordance with the invention in a range of from 0 to about 100 mol %, and preferably 0 to about 15 mol % to provide particles that have preferred elasticity, density and mechanical stability properties.

The particles formed according to this Example having a barium sulfate load inside the core were then esterified according to Example 16 and vacuum-dried. 300 g of the dry beads were suspended in 300 g water which was completely absorbed by the polymethacrylate cores within less than 1 min while the barium sulfate powdered particle surface appeared dry and the particles showed no tendency to agglomerate.

The particles (now 600 g) with 50 weight percent (wt %) water inside were spray coated with APTMS/PTFEP in an MP-1 Precision Coater™ fluidized bed coating apparatus according to Example 18 with the exception that an additional aminosilane adhesion promoter was used. The process equipment used was the same as that of Example 18, but the coating provided included three different layers. A bottom coating of 3-aminopropyltrimethoxysilane (APTMS) adhesion promoter was provided upon which was a second coating layer of a mixture of APTMS and PTFEP and a third, top coating layer of PTFEP. All three spray solutions were prepared by dissolving the coating material in isopentyl acetate and ethyl acetate in a 1:1 weight percentage ratio mixture. The first solution included 35 µl APTMS dissolved in 200 g acetate mixture. The second solution included 25 µl APTMS and 125 mg PTFEP in 150 mg of the acetate mixture and the third included 50 mg PTFEP in 60 g of the acetate mixture. The spray solution quantities and concentrations refer to the coating of a 300 g batch with 350 µm particles. The absorbed water evaporated at a rate of 5-10 g/min. The process was stopped after 30 min when the coating thickness reached 100 nm and the residual water content was 18.4 wt %.

Example 22

The absorption of organic dyes was tested on microparticles formed according to Example 15. To 2 ml of phosphate buffered saline solution containing 1 ml of hydrated beads was provided an amount of 5-10 µl of the respective dye as a 10 millimolar solution in ethanol. The samples were incubated for 30-60 minutes at room temperature under gentle shaking of the vial. Supernatant liquid was discarded and particles were washed three times with 2 ml of either deionized water, saline or PBS buffer solution prior to visualization with optical and fluorescence microscopy. The dyes tested included triphenylmethane derived dyes such as Fluorescein diacetate and Rhodamin 6G which were evaluated along with carbocyanine based dyes such as DiI. The triphenylmethane based Fluorescein and Rhoamine dyes exhibited a specific affinity for the hydrophilic PMMA hydrogel core through ionic interactions. They were able to easily withstand the rigorous conditions of repeated washing and steam sterilization without substantial leaching.

The carbocyanine dye DiI on the other hand exhibited a high selectivity for the hydrophobic PTFEP shell, without penetrating the hydrophilic PMMA core material. Thus with the subsequent staining employing the combination of DiI and Fluorescein diacetate both core and shell could be simultaneously visualized employing a fluorescence optical microscope. As a result, this procedure provides a fast, sensitive fluorescence-staining assay for the PMAA particles that makes core and shell simultaneously visible under conditions encountered in actual application. It further enables assessment of the mechanical-elastic stress or damage to the PTFEP shell. It further shows the affinity of certain classes of dyes for the various components of the particle.

It will be appreciated by those possessing ordinary skill in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of tracing the passage of a particle through a blood vessel in a mammal, the method comprising injecting into the bloodstream of a mammal at least one tracer particle, the tracer particle comprising poly[bis(trifluoroethoxy)phosphazene] and/or a derivative thereof and a contrast agent, and imaging the route of the particle.

2. The method according to claim 1, wherein the tracer particle comprises a core and a coating surrounding the core, wherein the coating comprises poly[bis(trifluoroethoxy)phosphazene] and/or a derivative thereof and the core comprises an acrylic-based polymer hydrogel.

3. The method according to claim 2, wherein the particle core further comprises barium sulfate as coating and/or diffused within the core.

4. The method according to claim 1, wherein the contrast agent is selected from the group consisting of barium sulfate, tantalum compounds, gadolinium compounds and iodine-containing compounds.

* * * * *

UNITED STATES PATENT AND TRADEMARK OFFICE
CERTIFICATE OF CORRECTION

PATENT NO. : 9,511,153 B2
APPLICATION NO. : 13/623151
DATED : December 6, 2016
INVENTOR(S) : Harder et al.

It is certified that error appears in the above-identified patent and that said Letters Patent is hereby corrected as shown below:

On the Title Page

Column 1, Item (60), Line 1, please delete "Provisional Application No. 60/684,309" and insert --Provisional Application No. 60/684,307"--

Signed and Sealed this
Fifth Day of March, 2019

Andrei Iancu
*Director of the United States Patent and Trademark Office*